United States Patent
Hageman

(10) Patent No.: US 9,795,628 B2
(45) Date of Patent: Oct. 24, 2017

(54) PRODUCT FOR USE IN THE PROPHYLACTIC OR THERAPEUTIC TREATMENT OF A NEGATIVE EMOTION OR INTROVERT BEHAVIOUR

(71) Applicant: N.V. Nutricia, Zoetermeer (NL)

(72) Inventor: Robert Johan Joseph Hageman, Wageningen (NL)

(73) Assignee: N.V. Nutricia (NL)

( * ) Notice: Subject to any disclaimer, the term of this patent is extended or adjusted under 35 U.S.C. 154(b) by 0 days.

(21) Appl. No.: 14/412,782

(22) PCT Filed: Jul. 5, 2013

(86) PCT No.: PCT/NL2013/050507
§ 371 (c)(1),
(2) Date: Jan. 5, 2015

(87) PCT Pub. No.: WO2014/007636
PCT Pub. Date: Jan. 9, 2014

(65) Prior Publication Data
US 2015/0272982 A1    Oct. 1, 2015

(30) Foreign Application Priority Data

Jul. 5, 2012 (WO) ................ PCT/NL2012/050483

(51) Int. Cl.
| | | |
|---|---|---|
| A61K 31/715 | (2006.01) | |
| A61K 31/405 | (2006.01) | |
| A61K 38/02 | (2006.01) | |
| A23L 33/125 | (2016.01) | |
| A23L 33/17 | (2016.01) | |
| A23L 33/18 | (2016.01) | |
| A61K 31/717 | (2006.01) | |
| A23L 33/10 | (2016.01) | |
| A61K 31/138 | (2006.01) | |
| A61K 36/899 | (2006.01) | |
| A61K 31/343 | (2006.01) | |
| A61K 38/08 | (2006.01) | |
| A61K 31/716 | (2006.01) | |
| A61K 31/718 | (2006.01) | |
| A61K 31/202 | (2006.01) | |
| A23L 33/00 | (2016.01) | |
| A23L 33/175 | (2016.01) | |
| A23L 33/21 | (2016.01) | |
| A23L 33/22 | (2016.01) | |
| A23L 33/24 | (2016.01) | |

(52) U.S. Cl.
CPC ............ *A61K 31/717* (2013.01); *A23L 33/10* (2016.08); *A23L 33/175* (2016.08); *A23L 33/18* (2016.08); *A23L 33/21* (2016.08); *A23L 33/22* (2016.08); *A23L 33/24* (2016.08); *A23L 33/30* (2016.08); *A23L 33/40* (2016.08); *A61K 31/138* (2013.01); *A61K 31/202* (2013.01); *A61K 31/343* (2013.01); *A61K 31/405* (2013.01); *A61K 31/716* (2013.01); *A61K 31/718* (2013.01); *A61K 36/899* (2013.01); *A61K 38/08* (2013.01); *A23V 2002/00* (2013.01)

(58) Field of Classification Search
CPC .... A61K 31/715; A61K 31/405; A61K 38/02; A23L 33/125; A23L 33/17; A23L 33/18
See application file for complete search history.

(56) References Cited

U.S. PATENT DOCUMENTS

| | | |
|---|---|---|
| 2005/0256031 A1 | 11/2005 | Hageman et al. |
| 2006/0040003 A1 | 2/2006 | Needleman et al. |
| 2009/0203575 A1* | 8/2009 | LeBowitz .............. A61K 38/30 514/1.1 |

FOREIGN PATENT DOCUMENTS

| | | |
|---|---|---|
| CN | 102488012 A | 6/2012 |
| JP | H04506080 A | 10/1992 |
| WO | 9955174 A1 | 11/1999 |
| WO | 0141581 A1 | 6/2001 |
| WO | 2005060952 A1 | 7/2005 |
| WO | 2007070454 A2 | 6/2007 |

OTHER PUBLICATIONS

Sindayikengera et al., J. Zhejiang Univ. Science B, 2006, 7(2), p. 90-98.*
Gourbeyre et al., J. Leuk. Bio., 2011, 89(5), p. 685-695.*
Ball et al., J. Nutr., 1984, 114(10), p. 1741-1746, abstract only.*
Walton et al., Br. J. Nutr., 1984, 51, p. 279-287.*
Leek et al., Anim. Feed Sci. Technol., 2007, 135, p. 86-99.*
Office Action issued for corresponding Russian Patent Application No. 201380046443.8, dated Dec. 23, 2015.
Zheng et al., The Enzyme-Resistant Property and Physiological Function of Cassava Cross-Linked and Esterfied Maltodextrin, Food and Fermentation Industries, vol. 34, No. 3, Dec. 31, 2008, pp. 11-14.

* cited by examiner

*Primary Examiner* — Jonathan S Lau
(74) *Attorney, Agent, or Firm* — Banner & Witcoff, Ltd.

(57) ABSTRACT

The invention relates to a nutritional composition comprising dietary fiber, a peptide having 7 or more amino acid units, the nutritional composition comprising a tryptophan source, which may be said peptide or different there from, for use in the treatment of a negative emotion or introvert behavior. The invention further relates to a combination of dietary fiber, a peptide having 7 or more amino acid units, the nutritional composition comprising a tryptophan source, which may be said peptide or different there from, and optionally one or more other components, for use in the treatment of a negative emotion or introvert behavior.

11 Claims, 1 Drawing Sheet

PRODUCT FOR USE IN THE PROPHYLACTIC OR THERAPEUTIC TREATMENT OF A NEGATIVE EMOTION OR INTROVERT BEHAVIOUR

RELATED APPLICATION DATA

This application is a National Stage Application under 35 U.S.C. 371 of co-pending PCT application PCT/NL2013/050507 designating the United States and filed Jul. 5, 2013; which claims the benefit of PCT application number PCT/NL2012/050483 and filed Jul. 5, 2012 each of which are hereby incorporated by reference in their entireties.

The invention is in the field of nutritional products and their medical use. The invention in particular relates to dietary fibre for use in a number of treatments of a subject that suffers from a disorder of the nervous system, in particular to dietary fibre for use in combination with a tryptophan source.

Serotonin is an important neurotransmitter of the nervous system in humans. Impairment of serotonin signalling systems is common in individuals, which suffer from behavioural or mental disorders. An example of serotonin signalling systems are those in the central nervous system (CNS), the so called central serotonergic system. Malfunction of the central serotonergic system in individuals is thought to contribute to etiology and pathology of this group of individuals. Serotonin is also an important neurotransmitter in the enteric nervous system and functions as a signal substance in the gut tissue and mucosa, as it is released in relatively large quantities by enterochromaffin cells that are present in the epithelial lining of the intestine.

This impairment of central serotonergic (5HT) systems can in particular be observed in those individuals demonstrating negative emotionality and introvert behaviour, which contributes to the pathology in a wide range of mood and behavioural disorders, like during clinical depression, autism spectrum syndrome (ASD), during anxiety disorders, phobias and bipolar disorders, during affect disorders, addiction, lethargy and avoidant—or obsessive-compulsive behaviour. These disorders are common in society and a proper treatment to alleviate symptoms or cure the disorders is desirable.

The impairment of the serotonin systems during these pathologies may include an abnormal release pattern of serotonine as a reaction to activation to presynaptic neurons or enterochromaffin cells, it may include an abnormal response of postsynaptic neurons to synaptic serotonin or systemic serotonin, may include an abnormal expression of serotonin receptors over tissue or over neuronal membranes, and may include an abnormal response of serotonergic neurons in neural networks. Parts of such impairment may be induced by increased systemic concentrations of cortisol and cytokines, which phenomenon is sometimes reported to be associated with several of the pathologic symptoms that are subject of the invention. The release of several cytokines and cortisol is also associated with the release of interferon-gamma by immune cells like T cells and natural killer cells. This is thought to increase the catabolic kynurenine pathway of tryptophan, in particular by increasing the activity of indole 2,3 dioxygenase in the diseased tissues. This can decrease endogenous tryptophan—and central serotonin concentrations to undesired low levels.

A known measure to treat forms of negative emotionality is to administer selective serotonin reuptake inhibitors (SSRI's), or (less common) monoamine oxidase (MAO) inhibitors. These drugs are designed to improve serotonin signalling, but unfortunately appear not to be effective in all individuals who are affected by such disorders. In addition in many individuals, SSRIs induce adverse effects after intake, despite the presumed selective nature of the drugs. An overdose of the drug may create a risk of the life-threatening serotonin syndrome, and one should take care to prevent adverse effects when specific drugs are co-administered. Side-effects of treatment include several symptoms which can be associated with excessive serotonin signalling in the central system (like anhedonia, apathy, fatigue, and somnolence) and induce symptoms associated with excess stimulation of the peripheral serotonergic systems (like sexual dysfunction, nausea, tremor, cardio toxicity and disturbed regulation of smooth muscle function). The disturbance in the regulation of smooth muscle function can apply to the blood vessels, which may cause blood pressure deviations, and to the smooth muscles in the gastrointestinal tract (GIT), which may cause gastroparesis, disorders in peristalsis and abnormal colonic movements. Such disorders may result in e.g. diarrhea and abdominal pain and discomfort, but also bloating, cramps and altered visceral perception.

Further, non-SSRI-type drugs have been prescribed. However, typically the latter appear to demonstrate a less favourable balance between efficacy and adverse effects than most SSRI's in the prescribed target population.

Also nutritional products have been proposed for treating mood disorders, for example until today several tryptophan-enriched formulae are commercially available.

WO 00/43013 relates to a formula that aims to treat serotonin-mediated disorder like a mood- or sleep disorder and comprises those particular types and quantities of components that make it suitable for use as infant formula, so for individuals younger than 1 year of age. This suitability applies to energy density, protein content and the amount and nature of fibre. These technical features do not make the product optimally suited for the treatment of negative emotionality or introversion in persons older than 1 year, and in particular older than 2 year, because the central nervous system and gut have changed to a large extent in the first year of life, and the metabolic pathways change as well as the nutritional requirements.

SUMMARY

It is an object of the present invention to provide a product (suitable) for prophylactic- or therapeutic treatment of one or more specific impairments, traits or disorders that are related to the functioning of the central nervous system (CNS). In particular, it is an object to provide such product which has a benefit, at least for a number of individuals, in that it provides a more effective treatment with respect to the intended use or a reduced severity, or duration or absence of an adverse side-effect that may be caused by a known product for the intended use.

This object is addressed by oral administration of a dietary compound, in particular in combination with one or more other dietary compounds for use in treating one or more specific impairments, traits or disorders that are related to the functioning of the central nervous system (CNS).

DETAILED DESCRIPTION

Figure 1:
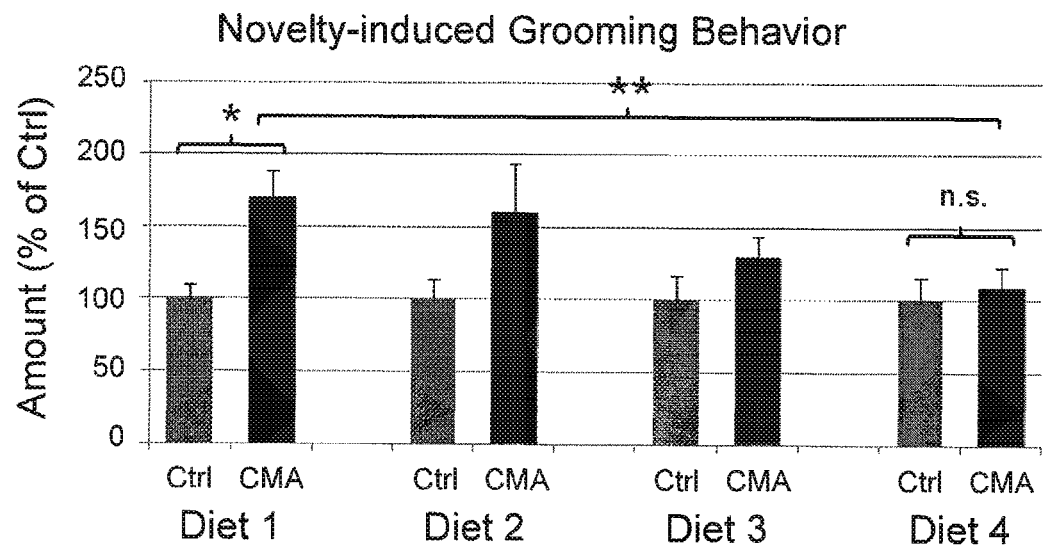
FIG. 1 depicts data directed to emotional disturbances induced by the CMA model and the effects of the dietary interventions.
Figure 2:
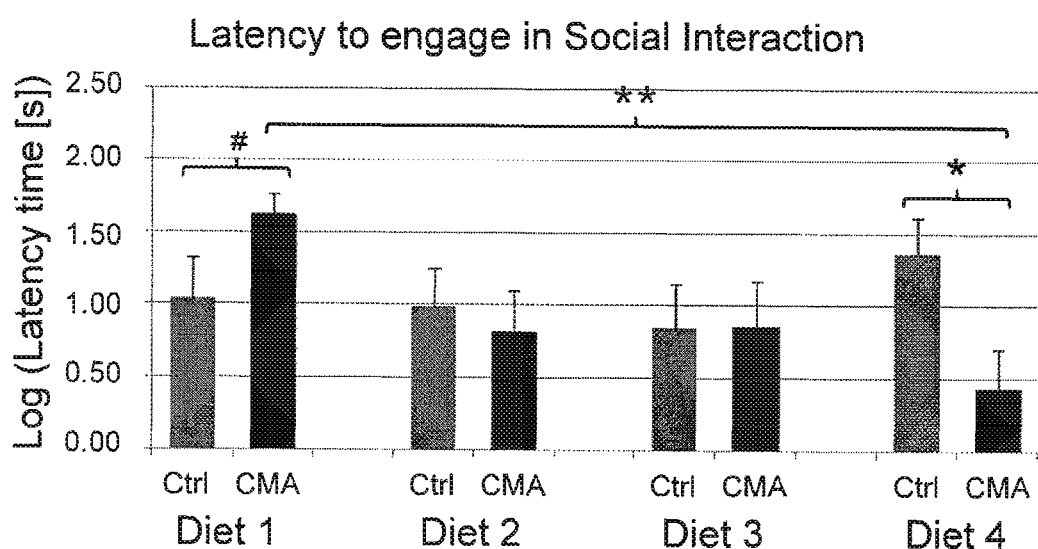
FIG. 2 depicts CMA-induced disturbances in social behaviour and the effects of the dietary interventions.

Accordingly, in an embodiment, the present invention relates to dietary fibre fraction and/or a protein fraction for use in the prophylactic or therapeutic treatment of an impairment of a serotonergic system in the central nervous system.

In a further embodiment, the invention relates to dietary fibre and/or a protein fraction, typically in an orally administered nutritional, product for use in the prophylactic or therapeutic treatment of a disorder selected from negative emotion, introvert behaviour, avoidant behaviour, and obsessive compulsive behaviour; preferably for use in the prophylactic or therapeutic treatment of a negative emotion disorder, more preferably for use in the prophylactic or therapeutic treatment of an introvert behaviour disorder.

In a further embodiment, the invention relates to dietary fibre and/or a protein fraction for use in the prophylactic or therapeutic treatment of a behavioural disorder, in particular a behavioural disorder selected from the group of pervasive disorders, clinical depression of major depression.

The protein fraction, more particularly the tryptophan, in any of such uses is in particular considered to have an effect in combination with the dietary fibres. Accordingly, the invention in particular relates to a combination of dietary fibre and a tryptophan source for use in any of said treatments according to the invention.

The combination of dietary fibre and tryptophan source may be administered sequentially, as part of a pharmaceutical preparation, or as part of a nutritional composition. In particular, the fibre and tryptophan source may form part of a nutritional composition.

Accordingly, the invention in particular relates to a nutritional composition comprising (as active ingredients) dietary fibre, and a protein fraction. The protein fraction will in particular be a tryptophan source and at least partially be a peptide comprising 7 or more amino acids, wherein the tryptophan source may be said peptide or be different there from. A nutritional composition may in particular be for any of said uses in accordance with the invention.

The dietary fibre—when administered to a human subject—may in particular be a dietary fibre that has an ameliorating effect on serotonin release by the enterochromaffin cells and/or enteric nervous system in the small intestine as a reaction to the postprandial luminal contents.

The dietary fibre may modulate the human microbiota as occurs in the small intestine, which may include bacteria, archaea and yeasts. In particular after oral administration of appropriate amounts of the dietary fibre or the product wherein the active dietary fibre is included, the type and activity of bacteria and archaea change, which inhabit the proximal part, more in particular those that inhabit the mucosa of duodenum, jejunum and proximal parts of the ileum. This may result in a lower amount of specific *Clostridia* species like the *histolyticum* and *tetani* types. The changed microbiota in the small intestine may also induce a better symbiosis between genera in the small intestine, and between host epithelial cells and mucosal microbial species. This may be reflected by a higher rate of synthesis or release of zwitter-ionic polysaccharides from locally present bacteria. An example of such polysaccharide is the polysaccharides that are synthesized by *Bacteroidetes* genera, in particular Polysaccharide A2. In one embodiment the product increases or normalizes the presence or activity of *Bacteroides fragilis*. In one embodiment the product increases the presence of *Bacteroidetes* in or near the mucosa of the small intestine, in particular that of *Bacteroides fragilis*. For clarity reasons: the polysaccharide as synthesized by the bacteria in the gut differs in chemical structure and identity from the polysaccharides that can be isolated from herbs like *Echinacea*, as disclosed in U.S. Pat. No. 4,857,512, though these polysaccharides may be included in certain embodiments of the invention.

In an embodiment the amount or activity of *Sutterella* genera as present in or near the ileal mucosa may decrease, as can be measured by determining species-specific RNA (e.g. the 16S rRNA) in faeces.

In an embodiment the product supports the development of those archaeon genera, which facilitate the colonisation of useful bacteria in the mucosa of the duodenum and proximal parts of the ileum. These archaea in the duodenum and ileum, and in the mucosa in these parts of the small intestine may differ from known colonic archeae, and from methanobrevibacter genera, as disclosed in e.g. WO2006102350. The symbiosis between archaea and mucosal bacteria is thought to be mediated by the secretion of adhesion modulating substances, glycolipids and polysaccharides that are released by archaea. The net effect of these changes may be the lower release of serotonin of locally present neurons and enterochromaffin cells, a decreased activation of the local enteric nervous system and/or a decreased degree of activation by the vagus nerve.

In one embodiment the modulation of types and relative abundance of microbiota in the gut is also observed in the colon. Such modulation can in one embodiment result in a more diverse population, which involves also Firmicutes, other *Bacteroidetes* phili than *Bacteroides fragilis*, Ruminoccaceae, Eubacteria, and *Faecalibacterium prausnitzi* and *Roseburia* species. Such increase in diversity in the colon can occur within the populations as occur within a one of the three specific enterotypes, as defined by Arumugam et al in Nature, 2011, vol 473, "Enterotypes of the human gut microbiome". Administration of the product according the invention increases the metabolic capacity of the population within a person belonging to a specific enterotype and modulates the fermentation patterns of fibres. This results in a lower sensitivity to develop negative emotions and introvert behaviour and decreases the risk of developing diarrhea, flatulence and cramps, and the induction of feelings of nausea and satiety after consumption of the diet. The diet also demonstrates a lower release by colon microbiota of putrefactive components, like indoles, phenols, sulfides and ammonia, despite the presence of the protein fraction in the product.

In one embodiment oral administration of the product according the invention is effective in those enterotypes which are characterised by a high metabolic activity of *Prevotella* or *Bacteroides* genera. In one embodiment administration results in a relative increase of the metabolic capacity or relative amount of Firmicutes genera. Methods for quantifying microorganisms are known in the art and include pyrosequencing and qPCR methods.

The presence of a more diverse and adapted community of microbiota in the small intestine facilitates efficient fermentation of dietetic fibres in more distal parts of the gut. The presence of a greater variety in metabolic capacity e.g. by the presence of specific *E coli* or Bifidobacteria variants may result in an early though partial hydrolysis of dietetic polysaccharides into (smaller) oligosaccharides. The smaller sized oligosaccharides are easier to access by other microbial enzymes, e.g. by hydrolases or feruloyl esterases. This allows generation of a different profile and wide diversity of fermentation products. These fermentation products may include for example ferulic acid, monosaccharides and small organic molecules which can interact with receptors on the membranes of epithelial cells or microbes. The active community of microbes in the mucosa also induces a higher expression of epithelial "brush border" di-saccharidases and hexose transporters, which facilitates absorption and use of nutrients from the intestinal lumen. The changed microbiome in the small intestine also decreases the amount of interferon-gamma that will be released as a result of luminal contents, which is thought to contribute to the lower activation of EC cells after administration of the product of the invention.

After consumption of a product in accordance with the invention, a more stable mucous layer is produced, which is more resistant to being flushed away due to excess serotonergic activity or due to diarrhoea, and which is not degraded excessively by intestinal microbes, like *Akkermansia muciniphila*, as is the case with prior art products which are used to promote central serotonergic systems or that are used in the treatment of negative emotions or introvert behaviour.

The fibre fraction may serve, at least for a part, as a nutrient for microflora in the small intestine. To the extent that the fibre fraction reaches, the colon, the fibre fraction will typically induce a change in colonic microflora. This change can be measured by proper sampling and analyzing of faeces or representative samples of mucosa or luminal contents of the proximal parts of the small intestine. This change is for example reflected by a higher ratio of the amount of the phylum *Bacteroidetes* to that of the phylum Firmicutes species. The ratio of the amounts of Firmicutes to that of Bacteriodetes as measured and calculated according the method of Mariat, et al, BMC Microbiology 2009, 9, 123, will become more normalized to reach a value of 1.5 to 14, preferably 3.4 to 13. Oral administration of a product in accordance with the invention may also decrease the amount of specific Firmicutes phylotypes e.g. *Clostridia perfringens,- histolyticum* or-*difficile*. The activity of other Firmicutes phylogenes like *Clostridia* species and other butyrate-generating species, like e.g. *Roseburia, Eubacterium* rectal and *Anaerostipes caccae* may be unaffected or even be increased. Van den Abbeele described in Env Microbiol 13 (10), 2667-2680 (2011) how the colonic flora of bacteria changes when rats are inoculated with human faecal bacteria and fed with arabinoxylans. No effect of the matrix was investigated nor the effect of a co-administered tryptophan source, nor an effect on the effect on the small intestine and the enterochromaffin cells located in the small intestine, nor the effect on negative emotions or introvert behaviour.

When referring herein to a treatment, this generally includes prophylactic treatments and therapeutic treatments, unless specified otherwise. A prophylactic (preventive) treatment generally is aimed at reducing the chance that the treated subject develops a trait, impairment, symptom, disease, syndrome or disorder. The effectiveness of a prophylactic treatment can e.g. be determined by comparing the probability that a specific trait, impairment, symptom, disease, syndrome or disorder develops in a sufficiently large, representative group of subjects or aninals in a double blind way according the principles of Good Clinical practices, wherein one part of the group is treated according to the invention and another part is treated with a placebo for a relevant period of time. The skilled person will be able to define suitable conditions for the study, depending on the intended effect.

The term "a" or "an" as used herein is defined as "at least one" unless specified otherwise.

When referring to a noun (e.g. a compound, an additive etc.) in the singular, the plural is meant to be included.

The term "or" as used herein is to be understood as "and/or" unless specified otherwise.

As used herein the term 'dietary fibre' is used for non-digestible oligosaccharides and polysaccharides having a degree of polymerisation of 3 or more. Non-digestible means that the saccharides are not digestible by human enzymes in the gastro-intestinal tract. Indigestible or partially digestible disaccharides are therefore not calculated as fibre. In a preferred embodiment these disaccharides are not added in the manufacture of a ready to use product according to the invention.

The dietary fibre fraction (or short 'dietary fibre') in a product according to the invention is usually a combination of different dietary fibre molecules. The dietary fibre molecules typically are carbohydrates that are at least substantially composed of a plurality of monosaccharide units. The dietary fibre molecules may differ in molecular weight, in chemical structure (such as difference in monosaccharide unit's composition, manner in which they are arranged in the molecule, difference in linkage between the monosaccharide units). A modified fibre may in particular be an enzymatically modified fibre, in particular modified with an enzyme that alters the structure or molecular weight of the fibre components.

When referred herein to the 'total fibre fraction' (TFF) this generally means the total of matter formed by dietary fibre. This includes the dietary fibre that is present as an active ingredient in the product, i.e. the dietary fibre that it is effective in contributing to an intended use of the invention (the 'active fibre') and other dietary fibre which does not have an effect on a claimed use, but may still have a dietary role. For instance, additional fibres having no significant role in the treatment of negative emotion and introvert behaviour can be included for technological or organoleptic reasons or to modulate colonic events. For instance, such fibre can serve as a bulking fibre (e.g. cellulose) or may induce envisaged colonic events.

With respect to the active fibre, these may in particular be selected from hemicelluloses, xylans and arabinoxylans When referred herein to a product in relation to the invention, this generally refers to a nutritional composition, combination of dietary fibre claimed as such or claimed for a use in accordance with the invention.

Mode of Action, Clinical Effects

The invention is in particular suitable to induce a selective way of modulating serotonin signalling and tryptophan metabolism in the body, and in particular to increase serotonergic systems in the central nervous system, but without inducing excessive serotonin-induced signalling of the enteric nervous system (ENS). In particular excessive serotonin release by the enterochromaffin cells and ENS neurons is prevented, especially in the lower parts of the GIT.

A fibre, combination or composition used in accordance with the invention can in particular contribute to changing the expression of serotonin receptors over tissues. In addition it changes the distribution and localization of the receptors per cell. The product also changes the degranulation and serotonin release characteristics of serotonergic neurons and EC cells. Without wanting to be bound by theory, this change can be mediated by an effect of the product on the activity of the nervus vagus, including the activity on the cholinergic transmission. Administration of the product according the invention will induce a secretion of serotonin that is sufficient to act synergistically with the cholecystokinine (CCK) that is released to activate the nervus vagus. Alternatively or in addition the effect on the serotonin systems may be mediated by a decreased action of bile acids on the lining of the small intestine or a modulation of the composition of the mucosal microflora and the response of the enterocytes, EC cells, enteroendocrine cells and dendritic cells, on microorganisms. This changed response may include an increase of the response of tolerizable genes, for example those that occur in macrophages inhabiting the small intestine or microglia, and are essential for a proper response after repeated exposure to microorganisms which induce the release of pro-inflammatory cytokines like IL-6. Some of the relevant genes have been disclosed in Foster et al, 20078, Nature, 447, 972-978 and include the Hdc, Mmp13, Serpine 1, Edn1, Cspg2, Lipg and Il6.

In one or more of these manners the administration of the product according the invention changes the functioning of the serotonergic systems, for example in terms of the release characteristics, the sensitivity to endogenously released 5-HT, the characteristics of the response and the desensitization characteristics. Such changes are not limited to the serotonergic neurons and EC cells, but apply also to those parts of the nervous system which are projections of the serotonergic neurons, like several dopaminergic- and noradrenergic systems, e.g. those in the central nervous system which are involved in the modulation of feelings of reward after exposure to a condition which is generally appreciated as satisfying, like touch, compliment, attention, warmth, and other forms that promote affect.

A fibre, combination or composition, used in accordance with the invention is in particular effective in the prevention and treatment of specific mood or behavioural disorders. Individuals who suffer from a pervasive failure to adapt to the demands of everyday life, e.g. by experiencing for more than 6 months significant problems in developing effective interpersonal functioning and demonstrate an impaired sense of self identity are the target group. Preferably the fibre, combination or composition is used in accordance with the invention in the treatment of an individual which can be classified as being of the avoidant- or the obsessive-convulsive type. Such personality types are in particular helped by ameliorating negative emotionality and introversion-symptoms.

Examples of the effect of the product include a better score in the trait domains 'negative emotionality' and 'introversion'. Methods are known in the art of psychiatry to assess reliably the degree of negative emotionality or introversion. For example a score can be given to the degree or severity of failure, based on observation of behaviour in standard- and test situations and questions/interviews. When for example in a range of 0-5, wherein 5 is the most severe pathology and a value of zero is absence of such behaviour, a score is obtained of 4 or more, the individual is diagnosed as a patient. The product will improve overall scores of negative emotionality and introversion. Dependent on the patient the improvement can be observed in any of the criterions which are used to determine the overall scoring. So the product can improve one or more of the group of excessive frequency or severity of the symptoms jealousy, anger/rage, envy, greed, guilt, shame, fear, arrogance, phobia, self pity, loneliness, feelings of inadequacy, pessimism, melancholy, worrying, feeling loss of control, lack of pleasure/anhedonia, lack of positive feelings/no desire to communicate with others, loss of affect.

During treatment it is preferred to take away the cause of the undesired behaviour, if possible, in order to have best results and prevent recurrence of the behaviour. So the fibre, combination or composition is preferably used in combination with a psychosocial intervention in the life of the subject treated in accordance with the invention. This could be a psychiatric treatment, or creating a change in the situation of daily life, wherein the exposure to the causes has been removed, decreased or modified.

The negative emotionality and/or introversion can for example be observed in persons who were diagnosed to suffer from one or more members of the group of depression, major depression, compulsive-obsessive disorder, an anxiety disorder, phobia, an autistic spectrum disorder, et cetera.

These effects are in particular observed in a person of 1 year of age or older, more in particular 2 years of age or older.

The efficacy of a use in accordance with the invention can be assessed by measuring the degree or severity of the disorder as existed before and after the intervention with the product. In addition the beneficial effect can appear because the incidence of the disorder has been decreased. This is especially the case when the disorder has an intermittent character, as is the case in several mood disorders, anxiety, phobia, lack of alertness and affects disorders.

The better score in negative emotionality and introversion can result in better scores in a wide range of tests, which also measure a range of other domains. For example the decrease in negative emotionality can result a better score in attention, affect, psychological stress, attention and anxiety. Reliable tests for measuring the degree or severity of a disorder in such attribute/domain/trait have been published in the art. As an example the psychometric tests of Table 1a can be used.

TABLE 1a

| Attribute/domain/trait | Test |
| --- | --- |
| Mood/affect Positive (enthusiasm, calmness) or Negative (confusion, depression, fatigue, tension) | Validated self-rating adjective checklists: POMS (profile of mood state), MAACL (multiple affect adjective checklist), PANAS (positive and negative affect schedule), VAMS (Bond-Lader visual analogue mood scales) Beck depression inventory, Hospital anxiety and depression scale |
| Psychological stress/tension | PSS (Perceived stress scale), DASS and other validated subscale of depression, anxiety or stress |
| Anxiety (perceived danger/misfortune) with symptoms of dysphoria/tension | Hamilton anxiety rating scale, STAI (state trait anxiety inventory, hospital anxiety and depression scale |
| Attention (ability to attend, select and use incoming information) Selective or sustained (vigilance) Alertness (enhanced arousal and readiness to receive and process information and respond | Visual selective search test, Stroop test, category search attention test, appropriate Event Related Potential (ARP) measures, TEA (test of everyday attention), CANTAB ( subtest of attention) Reaction time, speed of response to standardized tasks |

For more information in relation to the classification of mental diseases/disorders reference is made to DSM IV (Diagnostic and Statistical Manual of Mental Disorders, 4th Edition, Text Revision, also known as DSM-IV-TR, published by the American Psychiatric Association (APA));

Further, reference is made to ICD-10: cdc.gov/nchs/icd/icd10cm.htm; For negative emotions: dousa.nl/publications_depression.htm and brain.oxfordjournals.org/content/130/7/1732.full Further, reference is made to Example 5.

In a preferred embodiment the negative emotions belong to the group of feelings or sensations of alarm and fear, aversion and indifference, sorrow and grief and embarrassment. The tests as defined above allow the psychiatrist or health practitioner to quantify the degree and nature of these sensations and diagnose abnormalities. The handbooks like DSM and ICD give guidance aid in setting the criterions and diagnose the disorder or disease.

The invention aims to increase the feelings of joy and appreciation of the environmental circumstances and triggers to which the patients or individuals are exposed. Such triggers may for example be derived from food, social interactions and nature and encompass smells, tastes, temperature, touch, etc. This higher appreciation helps to decrease negative emotionalism and introvert behaviour, but also improves affect and social interactions.

This higher appreciation of environmental conditions, especially conditions which are appreciated as positive by normal individuals, is thought to be achieved by the better dopamine-mediated signalling processes, perhaps by the higher dopamine concentrations in the synapses or the higher sensitivity of the dopamine receptors, or the better integration of the dopamine signals in the mesolimbic systems of the brain, especially the nucleus accumbens.

Contrary to several prior art documents, which advocate the increase of kynurenine formation in order to decrease the negative effects of glutamatergic overexcitation and thus improve treatment of many types of diseases, the inventors believe that the amount of kynurenine must not be maximalized, but instead the route through quinolenic acid (QA), which is an agonist or activator of NMDA-mediated signalling, and therefore often called a "neurotoxin", should be higher. This means that tryptophan should be metabolized in a different way: increase of the flux through QA, at the cost of the part through QA.

Serotonin receptors are currently considered to be a group of 7 types of proteins. Each has its own distribution in the human body. Class 1 serotonin receptors are predominantly expressed in the central nervous system and not in the gastrointestinal tract (GIT), while e.g. class 2 and 3 serotonin receptors to an important extent determine the action of the serotonergic system in the gastrointestinal tract.

In particular, it is contemplated that in accordance with the invention a positive effect of the serotonergic system in the CNS, more in particular in the brain, while not activating the 5HT2 and 5HT3 receptors in the gastrointestinal tract or at least not to an undesirable extent.

Without wanting to be bound by theory, the inventors believe that at least two factors are important when achieving this. By inducing a redistribution of the 5HT1A receptors from soma to axonal—or synaptic parts of neurons, the desensitizing effects of the autoreceptor modus of these 1A receptors can decrease. The activation of postsynaptic 5HT1A receptors can subsequently occur by the increased amounts of serotonin that under the new conditions can be released. Secondly the invention may allow to change the distribution or localization of serotonin receptors that are not of the 5HT1 class, e.g. by increasing internalization mechanisms into endosomes, thus ensuring a more balanced serotonin response.

The better functioning of the postsynaptic 5HT1A receptors can be measured by applying methods known in the art, e.g. by measuring the kinetic properties of the receptor, but also by measuring the concentration of one or more products which are synthesized or metabolized by the cascade of reactions after 5HT1A activation. An alternative method is measuring the concentration of brain-derived neurotrophic factor (BDNF).

In particular, it is contemplated that the improvements in negative emotions and introvert behaviour in accordance with the invention will also result in better cognitive performance or social interactions.

Such improvement in cognition can be measured by subjecting the individual to a test, which measures the performance in the relevant domains, e.g. speed of correct recognition (memory) or speed of correct logical thinking. The Wechsler memory scale or ADAS-cog test or neuropsychological test battery and other tests have been used for persons having specific cognitive impairment. The man skilled in the art will know which test to use best under the given circumstances. This is likely to occur because of the effect of the product on the nicotinic receptors in the hippocampus.

In an embodiment, the improvement of negative emotions and introvert behaviour in accordance with the invention is also related to improvement in the development of obsessive compulsive behaviour in these patients. Tests for diagnosing obsessive compulsive behaviour have been disclosed in the art and include careful observation of behaviour, interviews with the environment including historic recording of events and bringing the individual in a (suggestive) test condition and observing his or her reaction.

In a specific embodiment, a negative emotions or introvert behaviour is treated in a person suffering from major depression, a bipolar disorder or suffering from a disorder in the autistic spectrum.

Fibre Fraction

In the text below a difference will be made between the fibre ingredient as used during manufacture, the pure fibre (the active molecule) and the total fibre fraction that is present in the product. The 'fibre ingredient' is the ingredient that is used to include the active fibre in the manufactured nutrition, nutritional product or ready to use medicament. It does not need to be provided as a pure ingredient, i.e. as a chemically pure compound. For example, the ingredient used for providing fibre in a product of the invention (the fibre ingredient), may still comprise other components than the fibre, that originate from the source from which the fibre ingredient is obtained, such as the germ or parts of the hull of a cereal from which the fibre ingredient is obtained. In particular, the ingredient used for providing fibre in a product of the invention may further comprise digestible carbohydrates, lipids and protein, but generally in an amount of less than 35 wt % of the fibre that is used in the nutritional product. Preferably the amount of digestible carbohydrates in the fibre ingredient is less than 24 wt %. The amount of resistant starch in the fibre ingredient may be up to 20 wt %.

Advantageously, the total fibre fraction in the nutritional product according the invention comprises fibre selected from the groups of modified and unmodified cereal fibre.

It is preferred that 10 wt. % or more of the fibre in the product is from cereal origin. Cereals in particular include plants belonging to the group of rice, wheat, rye, triticale, barley, oats, millet, amaranth and corn. Preferably the fibre in, or attached to or surrounding the grain is used for a product of the invention.

In a preferred embodiment the amount of the cereal grain based fibre fraction will be more than 40 wt %, more preferably more than 60 wt %, based on total fibre.

The fibre is preferably isolated from the cereal by treatment of the cereal grains. Preferably the fibre is isolated from the nucellar epidermis, the seed coat and/or pericarb of the cereal grain. Preferably, relatively low amounts of aleurone are used for the isolation of the fibre fraction. In a specific embodiment also the amount of endosperm that is co-isolated is low, which is reflected by a low amount of digestible carbohydrates in the isolated material. The proper fibres can be isolated from the cereal grain by applying a combination of methods on the raw ingredient, which are as such known in the art and can include grinding, sieving, extraction, steam treatment, alkali treatment and fermentation.

In a preferred embodiment, the active fibre comprises a xylan. The xylan preferably consists for more than 40 wt % of xylan-moieties, the remainder being one or more of arabinose- or glucuronic acid, or 4-methylated glucuronic acid or other monosaccharide moieties. These may originate from cereals. They can be linear or branched. In the preferred embodiment the xylans are at least branched for more than 10%, more preferably 13-60, most preferably 15-40 wt %, in order to decrease their rate of fermentation, gas production during their fermentation and be a more selective substrate for intestinal microorganisms. The branched xylans comprise more ferulic acid than linear xylans and in addition the changed structure of the xylans are thought to have different effects on diet-induced serotonin release in the gut, e.g. through a different bile acid mediated effect on the small intestine. This is associated with the absence of intestinal problems after consumption of the tryptophan source that aims to increase serotonin concentration in the brain.

In a preferred embodiment, the active fibre constituent, comprising xylan, or part thereof, is isolated by applying a treatment at alkaline pH or an extraction at such high pH. This treatment at alkaline pH may serve to solubilise digestible carbohydrates from the matrix to facilitate their removal in the preparation of the fibre isolate, but also allows breaking of the ester bond between hemicelluloses and lignin, as they occur in the raw grains. For the latter it is useful to add a reducing agent like sodium borohydride. This allows manufacture of a fibre ingredient which is relatively low in lignin and cellulose, relatively high in ferulic acid In particular, the fibres isolated from the cereal may be enriched in hemicellulose, compared to the total fibres content of the cereal from which the fibre originates. More in particular, the fibre fraction may be enriched in arabinoxylans.

Thus, the active fibre preferably comprises hemicellulose. The hemicellulose is preferably isolated from the hemicellulose fraction of cereal grains, though parts of the cellulose and lignin fractions can be co-isolated. More preferably, the hemicelluloses content is more than 45, more preferably 55 to 90 wt % of the fibre fraction.

Preferably, the active fibre comprises fibre, isolated from the hemicellulose fraction of cereal grains, though parts of the cellulose and lignin fractions can be co-isolated.

In particular, the dietary fibre may be composed for at least 11 wt. % of xylans, preferably about 13 to about 80 wt % of the fibre fraction.

Preferably the xylans are heterosaccharides. As used herein, the term leterosaccharides' is used for at least two different monosaccharide units. It is in particular preferred that more than 4 wt % of the xylan consists of saccharides other than xylose.

These heteroxylans in particular include arabinoxylans (AX). In a preferred embodiment, the active fibre comprises an arabinoxylan, present in an effective amount for use in the prophylactic or therapeutic treatment of a negative emotion or introvert behaviour In a specifically preferred embodiment, the arabinoxylans are branched, which ensures the formation of non-linear molecules. The arabinose substituents may make up from 0.05 to about 1 times the amount of xylose in the xylan. Part of the xylans may be (arabino)glucuronoxylans (AGX), glucuronoxylans or (glucurono)arabinoxylans (GAX), using the terminology of Ebringerova, et al, in Adv Polym Sci, 2005, 186, 1-67. The sum of AGX and GAX may be 0.4-30 times the amount of pure arabinoxylans. In a specific embodiment the amount of AGX is 0.5 to 24 times the amount AX.

In addition, or alternatively the xylan may comprise one or more other monosaccharide units other than arabinose in addition to xylose. In particular such unit may be selected from the group of uronic acid units, methylated uronic acid units, fucose units and galactose units.

One or more of the monosaccharide units in the xylan may be substituted with a phenolic compound, for instance like ferulic acid. In a preferred embodiment, the amount of ferulic acid in the fibre ingredient is 0.1 to about 6 wt. %. After (oral) administration of the product, a major part of the ferulic acid will in particular be released in the intestine, more in particular in proximal parts of the small intestine, by the action of intestinal enzymes, e.g. those originating from microorganisms.

In a specific embodiment, the xylans are partially hydrolysed prior to inclusion in the product in order to improve solubility in the ready to use product and to improve fermentability and effect of the product. In particular, a suitable degree of hydrolysis (DH) is 2 to 10. This can be achieved by applying an alkali treatment, an enzymatic hydrolysis or a fermentation process. In a preferred embodiment the enzymatic process includes a hydrolysis by a xylanase. Suitable sources of xylanase which are capable of hydrolysing cereal xylans are known in the art. In a preferred embodiment the fermentation step includes a step wherein the cereal fibre material is subjected to fermentation by a *lactobacillus* or a combination of a *lactobacillus* with yeast and optionally other microorganisms.

In particular, the dietary fibre in the product may comprise fibre selected from the group of unmodified or modified cereal fibre, isolated from the rice grain or rice kernel.

In particular, in the manufacture of the fibre ingredient one or more enzymatic hydrolysis steps can be applied to remove starchy material, e.g. with amylase or mixtures of enzymes that have glycolytic activity, or to break down the matrix to allow release of its constituents in the slurry of ingredient (like pullulanases, e.g. those isolated from bacteria as known in the art, cellulases or hemicellulases).

Further, an enzymatic treatment may involve the hydrolysis of polymeric fibre molecules into oligosaccharides. Examples of suitable enzymes include the xylanases (e.g. endoxylanases, e.g. derived from *bacilis subtilis*).

The active fibres according the invention are preferably isolated from the cereal by treatment of cereal grains. Preferably these fibres are isolated from the caryopsis and nucellar epidermis, the seed coat and/or embryo or germ of the cereal grain. The cereal fibre (ingredient) according the invention comprises therefore usually predominantly fibres derived from pericarp, tegumen, aleurone, scuttelum, epiblast and plumule. Preferably, the amount of fibres derived from these parts of the grain kernel are more than 85 wt % from the total fibre in the fibre ingredient. In a preferred embodiment the amount of aleurone-derived fibre and the amount of endosperm that is co-isolated is low, which is reflected by a low amount of digestible carbohydrates in the fibre ingredient. Preferably this amount is less than 36 weight % (=wt %), more preferably 20-32 wt % of the fibre ingredient. The amount of protein that is co-isolated with the fibres is 12-22, preferably 12-16 wt % of the fibre ingredient. Also lipids are present in the fibre ingredient to an extent of 14-24 wt % of the fibre ingredient. These amounts assume a moisture content of about 5 wt % of the ingredient. The concentrations of all components in the ingredient drop proportionally with its moisture content, while the properties remain the same when used in the manufacture of a liquid formula as those according the invention. The man skilled in the art can recalculate the amount of components to a moisture degree of 5% in order to establish whether a third party operates within the scope of this invention. Part of these cereal derived lipids, nitrogenous compounds and digestible carbohydrates are caught in the fibre structures as isolated from the grain and remain there to a characteristic and relevant extent during the manufacturing process of products according the invention.

A suitable fibre can be isolated from the cereal grain by applying a combination of methods to the raw ingredient, which as such are known in the art. They can include grinding, sieving, extraction, steam treatment, alkali treatment and fermentation. Several combinations have been used by different suppliers, though the final method for isolating the fibre according the invention is specific. In a preferred embodiment the active fibre constituents are isolated by applying a treatment at alkali pH or an extraction at alkali pH. This is applied to remove residual digestible carbohydrates.

Preferably the fibre ingredient as isolated from cereal grain comprises more than 40% hemicelluloses. Parts of the cellulose and lignins present in the grain can be co-isolated, though the contents of the sum of both in the fibre ingredient are less than 60%. Preferably the weight ratio of hemicellulose fibres to fibres that are considered as cellulose or lignin is more than 0.3, preferably 0.5 to 3, most preferably 0.6 to 2. In a further embodiment, the fibre comprises a dietary fibres selected from the group of gums, mucilage fibres, fractions from pulses, beans, oil seeds, roots, tubers, fruits, leafs, such as vegetable leafs, and synthetic oligosaccharides, like synthetic oligosaccharides based on fructose or galactose. Said fibres may be an additional source of active fibre (e.g. hemicelluloses, xylans or arabinoxylans from such a source) but may also provide another kind of fibre molecules, which may have a different purpose than the active fibre.

The gums are preferably selected from acacia gum, guar gum or chia gum. Preferably they are partially hydrolyzed saccharides derived from acacia gum and/or guar gum and/or chia plant gum. More preferably this hydrolysis is to a degree that more than 60 wt % of the gum fibre has a degree of polymerization of 3 to 20. This is in particular preferred in view of rheological considerations inside the gut, as a high content of intact gums may give rise to an undesirably high viscosity in the guts, even in the colon. This impairs digestion and increases the degree of activation of the sensing cells, when measured over the whole intestine. Preferably the amount of intact natural gum polysaccharides in the blend is therefore less than 20 wt % and more preferably less than 5 wt %, dependent on the nature of the gum. For example gum having a high degree of polymerization should be less than 5 wt % while gums that are significantly hydrolyzed to values of 15 or below, can be included in up to 20 wt % in the blend.

The weight percentage of gums, based on TFF, is usually 25 wt. % or less, in particular 2 to 18 wt. %

The tuber or root starch is preferably from a tuber or root selected from the group of onion, chicories, *beta vulgaris* (beetroot, sugar beet), potato, more preferably from chicory and beat.

The weight percentage, based on total fibres for fibres from a tuber or root in the TFF usually is 80 wt. % or less, preferably 5-60 wt. %, in particular 10-50 wt. %.

Suitable sources for fibre from pulses or beans are in particular soy beans, pea (e.g. *pisu sativum*) Azuki beans, *Phaseolus* varieties (e.g. *P. vulgarus*) and lupin seeds. Preferred sources are pea and soybeans. The weight percentage, based on total fibres for fibre from pulses or beans in the multifibre brend usually is 40 wt. % or less, in particular 2-30 wt. %.

Preferred sources for fibres from fruits or leaves from plants are plantain (including banana), prune, cabbage, tomato, squash, sugarcane, bagasse and citrus fruit. Particularly preferred is fibre from plantain, in particular banana. The weight percentage, based on total fibres for fibres from vegetable leaves or fruits in the usually is 40 wt. % or less, in particular 1-30 wt. %, more in particular 2-20 wt.

Suitable sources for resistant starch include cereals, for instance corn, wheat, rice, and tapioca and beans or pulses. The resistant starch preferably comprises resistant starch from rice. The weight percentage, based on total fibres, for resistant starch usually is 40 wt. % or less, in particular 3-35 wt. %. In particular, the resistant starch is present in a particulate form such, preferably comprising more than 80 wt % particles having a size of 2-15 micron.

Suitable fibres from oil seed include in particular, fibres from sun flower seeds and fibres from flax seeds. The weight percentage, based on total fibres for fibres from oil seeds, polydextrose (e.g. Litesse), oligosaccharides e.g. fructo or galacto-oligosaccharides in the multifibre blend usually is 40 wt. % or less, in particular 3-15 wt. %.

Commercial preparations for fibres from various sources are currently commercially available and include Sugar beet fibre from Nippon Beet Sugar being about ⅓ rd soluble Apple fibre (about ⅓rd soluble)

Chicory: raftiline

Soy fibre e.g. Fibrim

Resistant starch (Novelose)

Oat bran (about ½ soluble; Vitacel)

Commercial sources of oligosaccharides and resistant starch and their way of analysis have been disclosed in US2010/0317573, which is hereby incorporated as a reference.

A product according the invention comprises a dietary fibre which is derived from a cereal. It can be isolated as such, or be modified by chemical means to improve technological properties. The inclusion of unmodified fibre is preferred. The cereal fibre may be provided as chemically pure compound (e.g. chemically pure cereal arabinoxylan) or in a composition comprising one or more other compounds. A much preferred fibre ingredient providing the cereal fibre is cereal bran, in particular rice bran, either in raw form after physical separation of the starchy endosperm, or in more purified or processed forms.

In a preferred embodiment at least 10 wt %, more preferably more than 40 wt % of the dietary fibre is soluble in water at 20 degrees Celsius. In one embodiment more than 18 wt % of the fibre fraction is insoluble under these conditions.

The solubility of the cereal-derived fibre can be improved by treatment with one or more hydrolyzing enzymes selective for the carbohydrates, digestible or indigestible for humans, or the lipids present in the cereal fibre.

Alternatively the cereal fibre can be subjected to a fermentation process by exposing a slurry of the cereal fibre in water to one or more organisms or enzymes there from. A suitable fermentation process includes subjecting the fibre to the enzymes of an *Aspergillus* species. Fermentation processes for cereals are known in the art and help in improving solubility, by decreasing the molecular weight of the polysaccharides that form the indigestible part of the carbohydrates. A side effect is that the amount of digestible carbohydrates in the cereal fibre ingredient decreases.

In particular, the dietary fibre may be composed for at least 11 wt. % of xylans, preferably about 13 to about 80 wt % of the fibre fraction.

Preferably the xylans are hetero-saccharides, which are defined as being those oligomers or polymers of xylose that are substituted for more than 4 wt % with saccharides other than xylose. These hetero-xylans include arabino-xylans (AX). In one preferred embodiment the arabino-xylans are branched, which ensures the formation of non-linear molecules. The arabinose substituents may make up 0.05 to about 1 times the amount of xylose in the fibre. Part of the xylans may be (arabino)glucuronoxylans (AGX), glucuronoxylans or (glucurono)arabinoxylans (GAX), using the terminology of Ebringerova, et al, in Adv Polym Sci, 2005, 186, 1-67. The sum of AGX and GAX may be 0.4-30 times the amount of pure arabinoxylans. In one embodiment the amount of AGX is 0.5 to 24 times the amount AX.

The xylose moieties in the non-digestibe carbohydrate may also be substituted with monosaccharides other than arabinose, like uronic acids, methylated uronic acids, fucose and galactose.

One or more of the substituted monosacharides to the xylose oligomer may be substituted with phenolic compounds like ferulic acid. In a preferred embodiment the amount of ferulic acid in the fibre ingredient is 0.1 to about 6%. After oral administration of the product a major part of the ferulic acid will be released in the intestine, even in proximal parts of the small intestine, by the action of intestinal enzymes, e.g. those originating from microorganisms.

In one embodiment the xylans are partially hydrolysed prior to inclusion in the product in order to improve solubility in the ready to use product and to improve fermentability and effect of the product. A suitable degree of hydrolysis (DH) is 2 to 10. This can be achieved by applying an alkali treatment, an enzymatic hydrolysis or a fermentation process. In a preferred embodiment the enzymatic process includes a hydrolysis by a xylanase. Suitable sources of xylanase which are capable of hydrolysing cereal xylans are known in the art. In a preferred embodiment the fermentation step includes a step wherein the cereal fibre material is subjected to fermentation by a *lactobacillus* or a combination of a *lactobacillus* with yeast.

In a preferred embodiment the active fibre comprises arabino-xylans that have an average degree of polymerization that is at least 10% lower than in the natural grain, either by the application of the isolation process or by the enzymatic step. More preferably arabinoxylans which have a degree of polymerization between 3 to 18 make up more than 60 wt % of the arabinoxylans in the fibre ingredient. This facilitates its functionality in the small intestine.

The total fibre fraction in the ready to use dietetic or nutritional product according the invention may consist for more than 95 wt % of oligosaccharides having a degree of polymerisation of 3 or more.

As already mentioned the fibre is preferably isolated from the hemicellulose fraction of cereal grains, though parts of the cellulose and lignin fractions can be co-isolated. More preferably, the hemicelluloses fraction is more than 45, more preferably 55 to 90 wt % of the active fibre fraction. Other parts of the isolated fibre may be beta-glucans, which may amount to for example 0.5 to 10% of the total fibre fraction. Generally beta-glucans are not held responsible for the effect om EC cells in accordance with the invention.

The fibre ingredient may further comprise digestible carbohydrates, lipids and protein, but generally in an amount of less than 35 wt % of the fibre that is used in the nutritional product. Preferably the amount of digestible carbohydrates in the fibre ingredient is less than 24 wt %. The amount of resistant starch in the fibre ingredient may be up to 20 wt %

The active fibre fraction as disclosed above can in a further embodiment be combined with dietetic fibres from alternative sources like gums, mucilage, fractions from pulses, oil seeds, roots or vegetable leafs or be synthetic oligosaccharides like those based on fructose or galactose. The combination of all indigestible carbohydrates in the ready to use product makes the total fibre fraction (TFF) in the ready to use (RTU) product. However, in a preferred embodiment the amount of the cereal grain based fibre fraction will be more than 40 wt %, more preferably more than 60 wt %. This is in particular preferred for an embodiment wherein the fibre is part of a food supplement.

These alternative fibre fractions in the TFF may be included to improve other aspects of gut function. In particular this improvement is modulated by alternative mechanisms than ameliorating the activation of the enterochromaffin cells, especially those present in the proximal parts of the small intestine. These mechanisms may include improving colonic function, e.g. by increasing bulking of luminal contents, or modulating fermentation patterns in the colon.

Preferably the TFF includes soluble fibres based on mannans, like glucomannans, galactomannans, galactoglucomannans or other heterosaccharides based on a mannose oligomers or mannose polymers. These mannans can be isolated from for example guar gum or Konjac gum, by applying a specific combination of methods known in the art. It is preferred to have these mannans at least partially hydrolysed to arrive at fibre ingredient wherein more than 88 wt % of the oligosaccharides/polysaccharides have a degree of hydrolysis between 2 and 50. Suitable sources are commercially available and include for guar gum Benefibre and Sunfibre. The amount of mannans in TFF is in one embodiment more than 10 wt %, preferably 14-40 wt %.

In one embodiment the amount of indigestible homosaccharides, like inulin, fructo-oligosacchardes and galacto-oligosaccharides remains below 37 wt %, and is preferably less than 26 wt % in order to prevent over-activation of enterochromaffin cells.

In one embodiment the total fibre fraction in the RTU product comprises 2 to 50, preferably 3 to 40, more preferably 4 to 30 wt % galactans. These galactans are derived and isolated from gums like acacia gum. Preferably these galactans are heterosaccharides comprising at least more than 7 wt % non-galactose sugar moieties and more than 88 wt % may have a degree of polymerisation of 3 to 80.

In one embodiment the total fibre fraction in the product comprises little or no pectinic substances and/or added acidic oligosaccharides, in order to achieve the effect on the enterochromaffin cells and behaviour as disclosed in this patent application and prevent the release of too much acetate in the gut. Though some uronic acids will be present in the cereal fibre and natural fibres, as substituted to xylans or as minor constituents in the raw ingredient, the nature of such indigestible saccharides differs from added purified pectins as disclosed in WO2010147472. In particular the amount of added pectins, added pectin hydrolysates and added uronic acids is less than 40, preferably less than 10 wt % of the total fibre fraction in the product. In addition the product according the invention differs from that disclosed in the '472 document, because it comprises in a preferred embodiment no or relatively little D-ribose, in order to prevent undesirable discolorization of the product during heating and shelf life. The amount of added D-ribose is therefore less than 10, more preferably less than 2 wt %, and most preferably it is virtually absent.

The total fibre fraction (TFF) is formed by the total of all indigestible carbohydrates in a product, such as a nutritional composition in accordance to the invention, which may in particular be a ready to use (RTU) product. In an embodiment, the total fibre fraction in the (ready to use dietetic or) nutritional product (for use) according the invention consists for more than 95 wt % of oligosaccharides having a degree of polymerisation of 3 or more. Indigestible or partially digestible disaccharides are therefore not calculated as fibre.

The fibre fraction comprises fibre molecules that are effective as an active ingredient in a use in accordance with the invention, i.e. in a prophylactic or therapeutic treatment of a traits or disorder that is related to the functioning of the central nervous system (CNS), in particular in the prophylactic or therapeutic treatment of a negative emotion or introvert behaviour. These fibre molecules are herein below also referred to as 'active fibre'. Other fibres may be present, which generally of course will also have a function in a product of the invention. This function may reside in an in vitro effect or an in vivo effect. For instance, they may be present as a viscosity modifier (e.g. gums, uronic acids).

Advantageously, the dietary fibre (for use) in accordance with the invention allows modulation of processes in the gut, in particular the parts of the intestine downstream the ileum, including the colon. This modulation is thought to be a combination of factors, but is in particular thought to include the increase of release of beneficial amounts of specific compounds, such as butyrate by the gut flora (as a metabolite of fibre digested by the gut flora). Further, beneficial metabolites that may be formed by the gut flora include propionate.

This increase is thought to be achieved by a change in the fermentation pattern by the bacteria that occur in these parts of the gut or a change in the gut flora. It is in particular contemplated that the use of dietary fibre, a combination or nutritional composition in accordance with the invention contributes induce one or more effects in the gut, which surprisingly are beneficial with respect to a use according to the invention, which is related to the CNS.

In particular, a dietary fibre is provided that is effective in decreasing the release of serotonin in the gut under physiological and stressed situations. This applies to the release of 5HT after consumption of the product compared to prior art products, which intend to improve central serotonergic subsystems. It also applies to other nutritional products that are to be consumed by the patient during that same day.

In an embodiment of the invention, the dietary fibre has a prebiotic index below 4.2. (as defined by Roberfroid 2007). The relatively low prebiotic index reflects that the product does not achieve its effect on behaviour by maximizing its prebiotic potential as suggested by WO2010/147472 for a blend of fibre, including acidic oligosaccharides and rice bran, baker's yeast and D-ribose to inhibit virus replication and by EP-B 1383514 to decrease inflammatory processes and activate non-specific immune parameters by a blend of fructo-oligosacharides and inulin, and by WO02/060279 which aims to induce a prebiotic effect by oral administration of alpha-lactalbumin.

In an embodiment of the invention, the fibre may also demonstrate a relatively low prebiotic effect with respect to those bacteria that are adhered to the mucosa of the small intestine.

The mucosa-associated microbial community in the small intestine can be measured by applying the ProDigest or LabMET methodologies as are known in the art (e.g. from WO2011/060123). The adhesion-related prebiotic index may be less than 8.0, preferably less than 7.2, using the calculation method as disclosed in Van den Abbeele, et al, Appl Microbiol Biotechnol 2009, in Horremans et al *Helicobacter* 2012, or equivalent method. The adhesion characteristics of microorganisms can be further determined in vitro by applying an in vitro gut cell model, for example the Caco-2 cell based model as disclosed by Grootaert et al J Microbiol Meth 2011, 86 (1), 33-41 al alternative methods.

The change in colonic microbiota, which can be induced by the dietary fibre, may facilitate the growth of those microorganisms which generate fermentation products which are beneficial to the colonic epithelium like propionate, butyrate, lactate and other ferments, while generating slowly a relatively low amount of gas, including nitrogen, carbon dioxide, methane, ammonia and hydrogen sulphide. The latter effect decreases the prevalence of flatulence after oral consumption of the product.

Advantageously, dietary fibre is provided wherein the fibre—when administered to a subject—results in a stimulation of the GPR43 receptor (the G-protein coupled receptor −43). This is probably achieved partly through the release of a high ratio of the weight amounts of butyrate to acetate, of the weight amounts of the sum of butyrate+propionate to that of acetate and to the low rate of acetate generation over the relevant regions of the colon and the distal ileum. The latter is important because it prevents the impairment induced by high acetate (>10 mM) which can easily be achieved in the lumen by applying acetogenic fibres, whereby the concentrations of propionate and butyrate in blood remain to low to activate GPR43 or GPR41 receptors.

In particular, a fibre for use in accordance with the invention generates also such profile of fermentation that the GPR41, as for example is expressed in the sympathetic ganglia in the nervous system are not strongly activated, which decreases the signalling through the spinal sympathetic nerves to the CNS. This prevents over-activation of the sympathetic nervous system and diarrhoea.

In particular, the fibre fraction induces the reactions on enteroendocrine (EE) and enterochromaffin cells (EC) cells and on the sympathetic system. The release of the short chain fatty acids (SCFA's) is preferably caused by an increase of butyrate release by non-pathogenic bacteria, *Eubacterium limosum* being one of them. The increase of this bacterium allows *Bifidobacterium longum* to increase its capacity to synthesize or release butyrate.

The increase of SCFA synthesis in the lower GIT is observed in both females and males and the increase in the ratio of butyrate to acetate of more than 10% is observed in especially in persons having a body mass index of less than 25 kg/m2 and especially in the male population.

The amounts of gases that are produced during fermentation are relatively low. This applies to the sum of hydrogen, methane and nitrogen. The amount of ammonia that is excreted in the faeces increases.

The different pattern of free fatty acids that are released by mucosal bacteria in the small intestine activate differentially the free fatty acid receptors that are present in the gut, like the chemoattractant receptor GPR43. The minimum degree of activation after oral administration of the dietary fibre—when administered to a subject ensures a proper immune reaction during the intense communication between microorganisms, as present in the mucosa of the small intestine, and the neighbouring epithelial cells, in particular enterochromaffin cells. The communication may include activation of serotonin receptors but also Toll-like receptors and Nucleotide-binding oligomerization domain-like receptors, like for example NOD-2, which in one embodiment all maintain an activated state after oral administration of the fibre fraction. It has to be noted that the nature of luminal bacteria can differ from mucosal bacteria and mucosal microorganisms.

After oral consumption of the product the need for a high activity of T-helper 17 cells is decreased, which increases the balance between the IL-10 producing regulatory T cells and the Th17 cells in the GIT of the child or adult, though it maintains a sound release of IL-12 by dendritic cells in the gut to maintain a Th1 response, when required, e.g. to combat opportunistic infections by pathogens that may have entered the gut or developed in the lumen. The new balance between immune cells in the gut, especially in the small intestine, decreases the release of interferon-gamma and maintains the concentration of tryptophan in the intestine on a properly high level and keeps the concentrations of potentially damaging tryptophan catabolites low.

In particular it is preferred that the fibre after consumption by the patient will generate during fermentation in the colon one or more non-acetate metabolites, in particular butyrate or propionate. The weight ratio of the sum of [butyrate+propionate] to that of acetate as is produced in the colon after intake of a product in accordance with the invention—comprising active fibre and optionally further fibre molecules—is advantageously larger than 0.2, preferably more than 0.25, more preferably 0.27 or more. The weight ratio of [butyrate+propionate] to acetate may in particular be 0.61 or less, more in particular 0.56 or less, or be 0.4 or less. It is considered beneficial that under stress conditions succinate or lactate is synthesized as well in the colon, however at such low concentrations that no excessive excitation of serotonergic systems in the colon is induced. One of the butyrate generating classes of organisms in the colon is the group of *Clostridia* species. Induction of specific *Clostridium* clusters in the colon of the patient is considered by the inventors to be beneficial in the treatment of mood and behavioural disorders, in particular pervasive disorders, perhaps by inducing regulatory T cells in the gut which improve the immune system in the gut. Promotion of growth of *Clostridia* clusters IV and XIV could play a significant and positive role for both efficacy and prevention of adverse effects of the treatment as claimed.

This view differs from the view in the art wherein promotion of lactobacilli and prevention of *Clostridia* was said to be beneficial in the treatment of autism spectrum disorders or depression.

Suitable fibres from oil seed include in particular, fibres from sun flower seeds and fibres from flax seeds. Suitable fibres from roots include in particular beet fibres. Suitable fibres from fruits in particular include fibres from plantains, more in particular bananas. Suitable fibres from pulses include in particular fibres from lupin and soy. Synthetic oligosaccharides may in particular those comprising fructose units or galactose units. A fibre from any of said sources is preferably used with an active fibre selected from the cereal fibres, hemicelluloses, xylans and arabinoxylan, such as described herein.

One or more of these fibres in the TFF may be included to improve one or more aspects of gut function. In particular such improvement is modulated by alternative mechanisms than ameliorating the activation of the enterochromaffin cells, especially those present in the proximal parts of the small intestine. These mechanisms may include improving colonic function, e.g. by increasing bulking of luminal contents, or modulating fermentation patterns in the colon.

The fibre fraction usually comprises soluble fibre. Insoluble fibre may also be present.

In a preferred embodiment, at least 40 wt %, more preferably more than 60 wt % of the dietary fibre is soluble in water at 20 degrees Celsius.

The soluble fibre fraction preferably includes a beta-glucan or galactomannans originating from hydrolyzed or partially hydrolyzed guar gum. Preferably the soluble fraction comprises 15 wt % or more fibres selected from the group of beta-glucans, more preferably 18-90 wt %. This is thought to induce a total fermentation pattern that improves gut performance in treatment protocols meant to promote serotonin signalling in the brain.

Beta 1,3-glucans form a group of non-digestible carbohydrates which can be found in several types of ingredients. For example yeast, mushrooms, algae and several types of cereal fibres comprise them.

Beta-glucans is a diverse group of compounds, characterized that the main molecules have Beta-glycosydic bonds between D-glucose monosaccharides. Those present in some cereal fibres (e.g. in oats or barley) differ in physiological properties from those derived from e.g. yeast. In particular, a beta glucan from cereal, such as from oats or barley may contribute to an advantageous effect with respect to the treatment of a negative emotion or introvert behaviour. If present, beta-glucans from cereal preferably form 0.5-10 wt. % of the TFF. Optionally beta-glucans from non-cereal origin are added, in particular in a multifibre blend.

The beta-(1,3) glucans can comprise linear chains of monosaccharides which are predominantly connected to each other by a Beta 1-3 bond, and optionally partially by beta 1,6-, as occur in some yeasts, and/or optionally by beta 1,4 linkages, as occur in cereals or grains. The glucans can be linear or be substituted with for example other saccharides, with peptides or amino acids, and/or with lipids or fatty acids and can be soluble or insoluble in natural conditions. They can have a wide range of molecular weight and occur in several special forms, which each demonstrate different properties and biological activities. Of special interest are beta 1,3 glucans which are partially substituted with saccharides which are linked by a beta 1,4 linkage to the beta 1,3 chain as occur in cereal and grain fibre. In nature they typically occur to a high extent as insoluble globules which can be recognized under microscopy as particles which can have a diameter of 10 micrometer. Disruption of these globules is useful to make them soluble and to increase biological effective. Sonification and high shear or high pressure homogenization are suitable techniques to achieve this. The beta-(1,3) glucan molecules can absorb several times their molar amounts of water and commercial dry preparations demonstrate different degrees of dehydration.

The total dietary fibre in the product preferably comprises insoluble fibre. Such fibre induces a specific fermentation pattern, due to the different types of bacteria that preferentially will start to grow. In particular, it may contribute to a favourable production of metabolites other than acetate in the colon.

If present, the insoluble fibre content, based on total fibres in the product, preferably is at least 8 wt %, more preferably 18 to 72 wt. %, in particular 22 to 58 wt %. Such high insoluble fibre contents are usually provided in a semi-solid- or solid product. The amount of insoluble fibre in the product can be selected to be higher if a more solid matrix is selected as vehicle for the active components to be administered.

In a specific embodiment, the insoluble fibres comprise resistant starch. In a preferred embodiment, the resistant starch is retrograded or RS3 starch. In a further preferred embodiment, the resistant starch fraction comprises more than 50 wt % linear polymers of alpha 1,4 glucans which have a degree of polymerization between 10 and 35. Suitable sources of such resistant starches are beans, peas, heat-treated potatoes and heat-treated cereals. Simultaneous presence in the colon of resistant starch and beta glucans, in combination with the xylans will support of growth of the right type of butyrate generating bacteria species. A preferred content of resistant starch in the fibre fraction is 3 wt % or more, more preferably 5-60 wt %, based on total fibre. Resistant starch is defined to be as those starches which remain intact after digestion during 2 hours in the system of Englyst et al Am J Clin Nutr 1999, 69, 448-454.

Preferably the TFF includes one or more soluble fibres based on mannans, like glucomannans, galactomannans, galactoglucomannans or other heterosaccharides based on a mannose oligomers or mannose polymers. These mannans can be isolated from for example guar gum or Konjac gum, by applying a specific combination of methods known in the art. It is preferred to have these mannans at least partially hydrolysed, whereby the mannan ingredient consists for more than 88 wt % of oligosaccharides having a degree of hydrolysis between 2 and 50.

Suitable sources for the mannans are commercially available and include for guar gum Benefibre and Sunfibre. The amount of mannans in TFF is in one embodiment more than 10 wt %, preferably 14-40 wt %.

In a specific embodiment, the amount of indigestible homo-saccharides, i.e. saccharides formed of a single type of monosaccharide units, like inulin, fructo-oligosacchardes and galacto-oligosaccharides is below 37 wt %. The content of indigestible homo-saccharides is preferably less than 26 wt %, in order to prevent overactivation of enterochromaffin cells.

In a specific embodiment the total fibre fraction in a (RTU) product (for use) according to the invention comprises 2 to 50, preferably 3 to 40, more preferably 4 to 30 wt % galactans. These galactans are usually derived and isolated from gums like acacia gum. Preferably these galactans are heterosaccharides comprising at least 7 wt % non-galactose sugar moieties. Preferably more than 88 wt % has a degree of polymerisation of 3 to 80.

In a specific embodiment the total fibre fraction in the product (for use) according to the invention comprises little or no pectinic substances and/or added acidic oligosaccharides, in order to achieve the effect on the enterochromaffin cells and behaviour as disclosed in this patent application and prevent the release of too much acetate in the gut. Though some uronic acids will usually be present in cereal fibre and other natural fibres, as substituted to xylans or as minor constituents in the raw ingredient, the nature of such indigestible saccharides generally differs from added purified pectins as disclosed in WO2010147472. In particular the amount of added pectins, added pectin hydrolysates and added uronic acids is less than 40 wt. %, preferably less than 10 wt % of the total fibre fraction in the product (for use) in accordance with the invention.

In addition the product (for use) according the invention comprises in a preferred embodiment no or relatively little D-ribose, in order to prevent undesirable decolourisation of the product during heating and shelf-life. The amount of added D-ribose is therefore preferably less than 10 wt. %, more preferably less than 2 wt %, and most preferably the product is essentially free of D-ribose.

The fibre may be free of acetogenic fibres, like inulin and fructo-oligosaccharides and of pectins or acidic homosaccharides which comprise less than 10% saccharides other than a uronic acid. The content of acetogenic fibres, if present, in the fibre fraction is usually less than 85 wt %, preferably less than 40 wt %, more preferably less than 10 wt % or the fibre fraction. This not only ensures a proper release of short chain fatty acids other than acetate, but also decreases the release of gases from the fermentation in the gut. This therefore also improves gastrointestinal comfort and decreases abdominal bloating, and flatulence. The inclusion of the claimed fibres from cereal origin, and the presence of the specific beta glucans, resistant starch and the specific xylans ensure this release of fatty acids while decreasing the amount of gas released in the gut during fermentation. The fermentation gases include hydrogen, methane, nitrogen and other gases. In an advantageous embodiment, administration of the fibres according the invention prevent also a decrease of faecal pH below a value of 7.0, preferably below 7.1, most preferably 7.15 to 7.5, as measured by determining acidity in the stool. This reflects the presence of a non-acetogenic microflora in the colon as a result of consuming the product.

In particular, the dietary fibre, combination or nutritional composition for use according to any of the preceding claims, wherein under conditions existing in the colon of a subject to which the fibre (in the combination, in the nutritional composition or in another form) is administered, at least part of the fibre is fermented thereby forming propionate, butyrate or acetate, wherein the ratio of the molar amounts of the sum of the amount of formed propionate plus butyrate to the amount of formed acetate is at least 0.2 and preferably in the range 0.25 to 0.61, most preferably in the range of 0.56 to 0.61. Such fermentation pattern may be induced by a modification of the gut flora by the diet, for example by a change in the ratio of the amounts of the phylum Firmicutes to *Bacteroidetes* to a ratio of more than 1.5, which could be especially beneficial to obese persons, having a body mass index of more than 25 kg/m$^2$.

The content of dietary fibre in a nutritional composition of the invention is usually at least 2 g per 100 g of the total nutritional composition, in particular at least 5 g per 100 gram, more in particular at least 6 g per 100 g. The content, in particular in a ready-to-eat product, is usually less than 50 g per 100 g, in particular 40 g per 100 g or less.

Usually, the total content of hemicellulose, including xylans (including heteroxylans, such as arabinoxylans) is at least 0.5 g per 100 g of the total nutritional composition, in particular at least 2.5 g per 100 gram, more in particular at least 5 g per 100 g. The total content of these fibres, in particular in a ready-to-eat product, is usually less than 50 g per 100 g, in particular 45 g per 100 g or less, more in particular, 35 per 100 g or less.

For a liquid product, the fibre content is preferably in the range of 2-15 g/100 g of the composition. For a semi-solid product, the fibre content is preferably in the range of 6-24 g/100 g of the composition. For a solid product, the fibre content is preferably in the range of 6-40 g/100 g of the composition Per day about 20 to about 1000 g of the product should preferably be consumed to induce the effect as desired. Typically the dose per day will be about 30 to about 400 g. This dose will typically be packaged in 1 to 10 portions to allow manufacture of ready to use package units. One embodiment is a liquid packed in a container of 30 to 125 ml volume.

The Protein Fraction

The protein fraction is defined to be the total mass of compounds that comprise more than 60 wt % amino acids in the molecule. Thus, it includes, free amino acids and its salts, esters of amino acids and (relatively short-chain) carboxylic acids, and peptides, including intact and hydrolyzed proteins.

When referred herein to amino acids, generally the proteinogenic amino acids are meant. Thus, when referring to doses of amino acids, the dose for the L-isomer is meant, except for glycine. Though the human body has a capacity to convert D-isomers to L-isomers, and racemic mixtures of amino acids could in some cases be useful in the context of the invention, the use of the L-isomers in the absence of D-isomers is preferred.

Advantageously, the protein fraction comprises a peptide having at least 7 amino acid units. Though this may induce an allergic reaction in persons suffering from an allergy for an epitope present in the protein fraction, the inclusion of such peptide is preferred, in order to decrease the need for inclusion of free amino acids and improve the taste of the product. This allows full compliance of the product according the invention by the envisaged subjects to be treated with a product according to the invention.

A tryptophan source is usually provided for use in combination with the (active) dietary fibre in the prophylactic or therapeutic treatment of an impairment in the central nervous system, in particular in a the prophylactic or therapeutic treatment of a negative emotion, introvert behaviour, avoidant behaviour, or obsessive compulsive behaviour. Tryptophan may be administered separately or together with the dietary fibre.

In an embodiment, the tryptophan source comprises free tryptophan, a salt thereof, an ester thereof, or compound having an amide or peptide bond to tryptophan, e.g. a dipeptide comprising a tryptophan unit The tryptophan content (including tryptophan present in bound form in peptides and other compounds comprising a tryptophan unit, such as an tryptophan ester) in a nutritional composition of the invention is generally 2 mg/g of the total composition or more, preferably 3 mg/g of the total composition or more. Usually the content is 6 mg/g or less, at least in liquid products. The content may be higher though, in particular in case the composition is a concentrate-product that is to be diluted before administration, e.g. reconstituted in water or blended with another nutritional product.

In an embodiment, the ratio of the weight of tryptophan to that of the large neutral amino acids leucine, isoleucine and valine in the protein fraction of the product is at least 0.22, preferably 0.23 to 20 and most preferably 0.28 to 4 Preferably the ratio of the weight of the sum of leucine plus isoleucine and valine to the weight of the sum of threonine, histidine and lysine is smaller than 2.8 preferably 0.8 to 2.4.

Advantageously, in a use of the invention, the dietary fibre and tryptophan are administered together as part of a nutritional composition. To this purpose, cereal fibre; rice fibre or a fibre similar thereto are in particularly advantageous.

The use of the dietary fibre, such as cereal fibre, which may be rice fibre, in combination with tryptophan is advantageous for an ample supply of rapidly available tryptophan to the blood compartment after oral intake and a low supply of other amino acids, which hinder passage of tryptophan over the blood brain barrier. So the amino acids in the dietetic product have a relatively high weight ratio of tryptophan to the sum of large amino acids, in particular to the large neutral amino acids (LNAA), i.e. the branched chain amino acids (leucine, isoleucine and valine), tyrosine and phenylalanine.

In particular for a nutritional composition for use according to the invention it is desirable that it is rapidly digestible. This ensures a relatively low exposure of the lower parts of the GIT to several components in the food and to dietetic tryptophan, compared to administering tryptophan in the form of slowly-digestible proteins.

In order to achieve this preferably (1) a protein fraction is used which comprises a high weight ratio of tryptophan to the sum of large neutral amino acids and/or (2) the product must allow easy digestion of the protein fraction. A high ratio is in particular a higher ratio than in a protein like casein. Suitable proteins include proteins isolated from whey, from plants (beans, seed, grains tubers, etc.), from fish, krill, animals (meat, skin, organs), algae, eggs and from mushrooms. Methods are known in the art to isolate protein fractions from these sources and include grinding and milling, sieving, dissolving and solubilising, extraction, separation and purification. Partial hydrolysis may improve technological properties of these ingredients.

Especially preferred are protein blends which comprise one or preferably two, more preferably three members of the group of pea protein, soy protein, fish protein, egg protein and whey protein.

In a preferred embodiment the proteins are present in their natural state in the product that is ready for consumption. Typically during manufacture of the protein ingredients, as well as during the manufacture of blended products which include these protein ingredients, the proteins therein are at least partially oxidized. This induces intramolecular- and intermolecular disulfide formation, which increases the globular character of proteins and hinders access or activity of digestive proteases like pepsin, trypsin and chymotrypsin. Therefore in a preferred embodiment, the in the protein fraction in a composition (for use) according the invention natural sulfhydryl bonds are still present for at least 20%, preferably at least 35%, most preferably at least 80%. This can be measured by measuring the amount of protein bound sulfhydryl moieties and comparing the value with the measured value of the protein ingredients as used in the manufacture of the product and obligatory declared on the label of the same product. The way that the proteins can be protected during manufacture of the ingredients or the ready to use product which comprises these protein ingredients are preferably selected from the group of 1/ preventing contact to oxygen by decreasing the time and extent to which these proteins can come into contact with atmospheric oxygen, 2/ preventing inclusion of oxidizing substances, 3/ decreasing the rate of reaction with oxidizing compounds, by optimizing heat treatment and avoidance of including catalyzing substances, like trace elements and redox active substances like anti-oxidants, and optionally 4/applying a separate reducing step when needed.

A relatively low degree of heating, of the product, and in particular of the protein fraction avoids denaturation of the protein. The presence of non-denatured protein in the product is contemplated to be beneficial in the nutritional management or other treatment of individuals suffering from negative emotions or introvert behaviour. Non-denatured proteins and peptides may demonstrate a better digestibility in the proximal parts of the intestine and thus improve uptake of tryptophan in the brain.

Thus, the inventors believe that during preparation or further processing of a composition comprising protein, it is advisable that attention is paid to prevent denaturation of protein. This can be done by applying an optimization of processing conditions, preventing excessive heating and the like. The degree of heat treatment which is applied to the product can for example be assessed by measuring Maillard components and the degree of browning. For the latter reason also the inclusion of reducing sugars, like ribose or fructose, especially in their monosaccharide form is preferably avoided.

Amino acid composition of the protein ingredients can be measured by applying methods known in the art, which include acid or alkali hydrolysis of peptide bonds in the protein, purification of the extract, chemical derivatization of the amino acids, chromatographic separation and detection of the individual components.

Preferably a protein is present that induces a postprandial response which includes neurological and endocrine effects in the gut and the enteric nervous system, which modulate satiety, nausea and the serotonergic systems involved in introvert behaviour and negative emotions. In addition it is preferred that the proteins will modulate the response of e.g. the pancreas to the systemic concentrations of glucose and amino acids. This induces e.g. a specific pattern of release of insulin and glucagon. These proteins are characterized by inducing a relatively high amount of glucagon compared to insulin, when compared to conventional protein blends which are used in casein-based medical food products.

The amino acid composition is preferably optimized to help such effects, in particular the effect on the response on the serotonergic systems. A relatively high amount of tryptophan to the sum of large neutral amino acids as been discussed above is therefore preferred.

In addition, it is preferred that the content of the sum of glutamate plus glutamine is preferably high in the protein fraction, in particular more than 18 g per 100 g protein fraction, more preferably 20 to 26 g per 100 g protein fraction, because this facilitates the functioning of the nervous systems in the gastrointestinal tract, in particular the serotonin-activated nervus vagus activity. In a specific embodiment glutamate or glutamine is present in a product of the invention, preferably in the range of 0.4 to 10 g per 100 g of the protein fraction.

The amount of cysteine equivalents is usually more than 1.7, preferably 1.8 to 2.8 g per 100 g of the protein fraction. This supports further the beneficial effect of the product on negative emotions and on introvert behaviour and allows sufficient release of hydrogen sulphide to modulate GIT response in case the product would be used in situations for persons who experience a partially inflamed gut. Suitable cysteine equivalents are cysteine, N-acylated forms of cysteine, like N-acetylcysteine and cysteine-rich peptides, like peptides from keratin or other cysteine-rich proteins, or specific proteins from egg or whey.

The amount of branched chain amino acids is preferably low to get the highest possible ratio of tryptophan to large neutral amino acids. So preferably a composition (for use) according to the invention is essentially free of free leucine, including a salt thereof.

Preferably a composition (for use) according to the invention is essentially free of added free proline, including a salt thereof.

The concentration of arginine in the product is preferably relatively high in order to facilitate the nitric oxide medicated activation of the nervus vagus. Preferably the amount of arginine in the protein fraction is more than 5, more preferably 5.4 to 9, most preferably 5.6 to 8 g arginine per 100 g of the protein fraction.

Proteins of plant origin, e.g. from cereals, like rye and wheat have a low weight ratio of tryptophan to the sum of large neutral amino acids. This means that the other proteins in the protein fraction of the product must comprise much tryptophan, or alternatively or additionally one or more other tryptophan sources should be used, such as free tryptophan (as acid, salt) or tryptophan-rich peptides. Preferably added free L-tryptophan as amino acid, its salt, its ester, or as an oligopeptide (i.e. a peptide having up to 10 amino acid units), in particular as dipeptide, preferably is provided in an amount of 0-12, more preferably 0.2 to 4 g L-tryptophan per 100 g of the protein fraction.

A product of the invention is usually essentially free of casein. If present, the casein content is typically less than 15 wt. %, preferably less than 2 wt % of the protein fraction.

The sum of dairy whey proteins and vegetable proteins is usually 5 to 100 wt %, preferably 22 to 98 wt % of the protein fraction.

In a specific embodiment, the ratio of the weight of vegetable protein (which is typically low in branched chain amino acids) compared to that of dairy protein, is at least 0.05 (wt/wt), preferably at least 0.2 (wt/wt).

A preferred protein fraction for use in a treatment of a person suffering from a mood- or behavioural disorder that is sensitive to food allergens meets the following features:
 tryptophan is more than 1.9 g per 100 g of the protein fraction
 the protein fraction comprises free L-tryptophan as amino acid, its salt, its ester, or as a peptide having 2-6 amino acid residues.
 5-95 wt %, based on the total protein fraction, of peptides have 2-6 amino acid units.

The dosage of protein is preferably relatively low, in particular less than 6 g per dose, preferably less than 5.5 g per dose, more preferably less than 4.9 g per dose. However, based on the contribution to the total energy the protein content in the (ready to use product) is preferably more than 18 en %, using the Atwater constants for the calculation. The latter is because other energy-providing components, in particular lipids,—if present—are preferably in a relatively low amount of in the product. Preferably the product has the form of a liquid or semi solid.

In a specific embodiment, the protein fraction comprises lysozyme as tryptophan source. The amount of lysozyme hydrolysate having a DH of less than 10, in this embodiment is usually less than 25 wt. %, preferably less than 20 wt %, more preferably less than 10 wt %, of the amount of lysozyme hydrolysate in the product which has a DH of more than 20. Preferably the amount of tryptophan polypeptides from hydrolyzed intact protein in the protein fraction is less than 1 wt %. Preferably the protein fraction comprises 80 wt % or less, and more preferably less than 30 wt % of hydrolysed protein, due to taste reasons.

In an advantageous embodiment, the protein fraction also contributes to the supporting role of the product as claimed on the functioning of the dopaminergic system. This system includes the release of dopamine when food is observed or briefly before it has to be consumed and can be measured as an increased appetite. In addition the supporting role comprises a better functioning of dopamine receptors, in particular the increase of the effect of dopamine which is released before or during the first stages of eating.

The protein fraction is preferably rapidly digestible, which prevents that lower EC cells release serotonin to a larger extent than the blood platelets can absorb and thus induce a satiating and nausea effect by activating 5HT3 receptors in the CTZ (chemoreceptor trigger zone) of the medulla.

The protein fraction preferably also induces a relative low CCK release by the 1-cells in the duodenum after consumption, because it generally comprises a low amount of kappa casein. The whey proteins, if present, therefore preferably comprise acid whey. More preferably acid whey is more than 40, most preferably 51-100 wt % of the whey proteins.

The liquid form of the product preferably is a homogeneous emulsion comprising at least a protein fraction, lipids carbohydrates, a fibre and a mineral fraction. The emulsion as such induces after consumption and passage of the stomach a release of cholecystokinin (CCK) which is relatively low, compared to prior art products.

The liquid composition preferably has a low buffer capacity. The phosphorous content in the (ready to administer) product is therefore preferably less than 14 mg, more preferably 3-13 mg per g protein fraction in the product. The product preferably has a relatively low amount of organic acids or is essentially free thereof. In a particular preferred embodiment the amount of organic acids which are typically declared as digestible carbohydrates on the label of the product is less than 5 wt %, preferably less than 2 wt % and more preferred less than 1 wt % of the digestible carbohydrate fraction.

This facilitates proteolysis of dietetic proteins of the product already in the stomach, predominantly by allowing rapid acidification of the gastric contents to the pH value which is closer to the optimum value for the proteolytic enzymes in the gut, including pepsin. This rapid pre-digestion also allows more rapid passage through the stomach pylorus and allows a more rapid neutralization of the digests that enter the duodenum. This decreases the release of CCK compared to conventional foods.

These effects on dopaminergic and serotonergic systems contribute to a desired eating behaviour in individuals in need of the product as claimed, because the full desired amounts of the product according the invention are consumed; in other words the compliance to the feeding protocol with the product as claimed is excellent, preferably more than 90%. Compliance with a desired level of intake of healthy nutrients is a major problem in the individuals suffering from the serotonergic disorders, depression, behavioural disorders and other diseases as mentioned in this document.

A superior digestion rate of a preferred composition of the invention, including the protein fraction can be accomplished in various ways. The selection of the type of protein has been discussed above. In addition it appears that the matrix of the product is important. It is therefore preferred to create a low buffer capacity in the ready to consume product. The phosphorous content in the ready to eat product is therefore preferably less than 14 mg, more preferably 3-13 mg per g protein fraction in the product. The pH of the product is in the range 3.0 to 7.4 and the osmolarity and viscosity is relatively low. The content of the protein fraction in a nutritional composition of the invention is usually at least 5 g per 100 g of the total nutritional composition, in particular at least 8 g per 100 gram, more in particular at least 14 g per 100 g. The content, in particular in a ready-to-eat product, is usually less than 50 g per 100 g, in particular 40 g per 100 g or less, more in particular 25 g per 100 g or less.

For a liquid product, the protein fraction content is preferably in the range of 5-9 g/100 g of the composition. For a semi-solid product the protein fraction content is preferably in the range of 8-20 g/100 g of the composition. For a solid product the protein fraction content is preferably in the range of 14-40 g/100 g of the composition.

The Digestible Carbohydrates

If present, the fraction of digestible carbohydrates preferably has a low glycemic index (GI). This ensures a small and slow increase of NADH in the cells of the gut, the nervous systems, immune cells and the liver. This is considered to be beneficial for maintaining proper redox potential in the cell, while at the same time generating a sufficiently large flux of reducing equivalents to the mitochondria of cells in the gut, immune cells and cells of the nervous systems in the gastrointestinal tract, the nervus vagus and the brain, to generate energy in the form of ATP (adenosine triphosphate).

It should be noted that in the prior art, it has been proposed to consume large amounts of rapidly digestible glucose sources in order to prevent muscle catabolism and increase brain serotonin biosynthesis (Wurtman, et al, 2003, Am J Clin Nutr 77, 128-132).

The speed of release of glucose moieties in the GIT is considered to be of large interest. The way to determine the GI value is known in the art and includes measuring glucose concentration in blood during the first 2 hours after oral administration of the product to be tested and and comparing the value of the area under the curve with that obtained after administration of glucose, which is assumed to have a value of 100. This can be determined by the method described in Englyst et g Am J Clin Nutr 1999, 69, 448-454.

The GI value of the digestible carbohydrate fraction is preferably less than 80, more preferably 20 to 72, most preferably 20 to 64. The GI value of the total digestible carbohydrate fraction complies with this criterion, though the various digestible carbohydrates in the total fraction may demonstrate different GI values, and some may even have a GI index above 64, or even above 80. It is desired that the amount of such individual digestible carbohydrates is also low. In particular the amount of free glucose in the total digestible carbohydrate fraction is preferably less than 10 wt %, more preferably less than 4 wt % in order to prevent a postprandial decrease of ghrelin release. The inventors consider a high ghrelin release after consumption of the product desirable, for example in order to increase digestion rate of the product.

The digestible carbohydrate fraction preferably comprises slowly- and rapidly digestible carbohydrate. The rapid digestible carbohydrates will keep rapidly the amount of systemic LNAA low in catabolic situations. However, for treatment of the negative emotionality and introversion and avoidant and obsessive-compulsive disorders the amount of rapidly digestible carbohydrates can remain limited. More than 3 times, preferably more than 4 times as much weight of slowly digestible carbohydrates should be included compared to the weight of rapidly digestible carbohydrates. His ensures a long lasting anti-catabolic effect and a good taste of the product.

Examples of such slowly digestible carbohydrates are some starches, some types of large pullulan oligomers, trehalose, isomaltulose, chemically modified carbohydrates and several residues of digestible carbohydrates, as present in the fibre fractions used in the product, such as the cereal fibre. The speed of digestibility of the ingredients included in the product can be measured by applying the standard method known in the art for this purpose: Englyst et al Am J Clin Nutr 1999, 69, 448-454. Those carbohydrates that are digested under these standard conditions to monosaccharide in the period between 20 and 120 minutes after the start of the experiment were considered to be slowly digestible. Those that were not yet digested at 120 minutes after the start were considered to be fibres.

The amount of digestible carbohydrates in the product usually is up to 8 times, preferably up to 5 times, most preferably less than 4 times the amount of protein in order to have the largest protein effect of the product. Especially when it is used as a supplement, the digestible carbohydrates will be consumed in high amounts anyway and excess digestible carbohydrates will impair the health of insulin-resistant individuals, like diabetics, many obese persons and many elderly. Insulin-resistance is strongly associated with the behavioural problems which are aimed to be treated by the product according the invention.

It is preferred that at least part of the carbohydrates origin from the fruits of the Musa genus. Plantains and bananas can be used as source of digestible carbohydrates and fibres. The fruits comprise different amount of rapidly digestible carbohydrates like sugars, dependent on the species and the degree of ripening of the fruit at the moment of measurement or use. A typical Cavendish banana will comprise about 12.2 g sugars (=about 53 wt % of total carbohydrates), 2.6 g fibre and about 8 g oligomeric and polymeric carbohydrates. The fruit-derived ingredients which are preferably used in the manufacture of the products according the invention comprise rapidly digestible sugars in an amount of less than 45 wt %, preferably less than 36 wt %, more preferably less than 18 wt % of the total carbohydrate fraction in the ingredient. Also the amount of rapidly digestible starch is low.

In a specific embodiment, the amount of banana-derived carbohydrates is between 1 and 70—preferably 2-60 wt % of the amount of digestible carbohydrates in the total product. Suitable ingredients include a puree of selected fruits or an extract of the fruit. Dependant on the final composition of the ready to use product different amounts of banana or different qualities can be used. The banana puree can be included in a content of 0.2 to 26 wt/vol % in the ready to use product.

The amount of digestible carbohydrates in a nutritional product (for use) according to the invention preferably is at least 8 wt. %, in particular 8-70 wt % of the total composition (in particular when present in a ready-to-eat form). The type of digestible carbohydrates is preferably selected on the criterion that the amount of rapidly available glucose sources is relatively low, while still creating a pleasant taste which is appreciated by the person that is to be treated in accordance with the invention in particular a person who suffers from a mood- or behavioural disorder or person who is consuming a product in accordance with the invention as a prophylactic measure to prevent occurrence of such disorder. Thus, the abundance of maltodextrins and glucose/fructose syrup, if present at all, is preferably relatively low.

In an advantageous embodiment, the nutritional composition comprises one or more slowly digestible ingredients, selected from the group of isomaltulose (or palatinose), isomaltose and trehalose.

A preferred blend of digestible carbohydrates in the treatment of a mood- or behavioural disorder complies with the following criterions:
1/ the sum of maltodextrins and glucose-fructose syrup is 2-90 wt %;
2/ lactose, galactose or banana puree >2 wt %;
3/ the sum of isomaltulose, trehalose and isomaltose >2 wt %;
4/ free fructose 1 to 8 wt %.

The type and amount of digestible carbohydrates appears to be important not only to provide a minimum amount of glucose and sweetness to the product to consume, but also to regulate the redox potential in intestinal cells, immune cells, liver cells and neurons. In an embodiment, a product according the invention aims to prevent excess formation of reducing equivalents, like NADH.

An improvement of the redox situation in the target tissue or target cells can be measured by measuring the weight ratio of NADH to NAD+, or of NADPH to NADP+ or of derived metabolites, like lactate to pyruvate, or oxidized glutathione to reduced glutathione, as known in the art. These values can be compared with values which are obtained after feeding under identical conditions the products as known in the art until now.

It is important that the amount of NADH in the cytosol of cells in the target tissue has become lower after feeding a dietary fibre, combination or nutritional composition according the invention. A lower value will result in the end in lower expression of stress proteins, like several heat shock proteins, for example of HSPA5, or alternative stress proteins like enolase 1 and GAPDH.

The content of the digestible carbohydrate fraction in a nutritional composition of the invention is usually at least 4 g per 100 g of the total nutritional composition, in particular at least 5 g per 100 gram, more in particular at least 8 g per 100 g. The content, in particular in a ready-to-eat product, is usually less than 80 g per 100 g, in particular 70 g per 100 g or less, more in particular 50 g per 100 g or less.

For a liquid product, the digestible carbohydrate content is preferably in the range of 1.5 to 9 g/100 g of the composition.

For a semi-solid product the digestible carbohydrate content is preferably in the range of 6-30 g/100 g of the composition. For a solid product the digestible carbohydrate content is preferably in the range of 16-70 g/100 g of the composition.

The Lipid Fraction

The amount of lipids in the nutritional composition is preferably relatively low in order to prevent a large post-prandial PYY- and CCK release. In a specific embodiment this amount is less than 4 g, preferably less than 3, more preferably less than 2 g, most preferably less than 1.7 g per dose.

The concentration nutritional composition will vary dependent on the intended serving size, but is typically less than 4 wt %. The contribution of the lipid fraction to the total energy as provided by the complete formula by its protein and digestible carbohydrates can be calculated, by using the Atwater calculation which assigned theoretical calculation factors of 16.7, 16.7 and 37.7 kJ per gram of respectively protein, digestible carbohydrates and lipids, and a contribution of zero to other food constituents. In the products according the invention the lipid fraction will typically be in the range of 1 to 35 en %, preferably 3 to 29 en %, more preferably 5 to 22 en %.

The lipid fraction preferably comprises more than 1, preferably 3 to 100, more preferably 6 to 60% of an oil comprising more than 2, preferably more than 20-g of the sum of eicosapentaenoic- and docosahexaenoic acid per 100 g fatty acids, in order to increase sensitivity of the receptors on EE cells, the EC cells and the central nervous system and the ENS but especially to increase dopamine release in the nucleus accumbens and striatal regions involved in reward sensation and motor neuron function. Important receptors which are sensitized by the product according the invention are G-protein coupled receptors on neurons. The effects of the product on membrane functioning result in better localization of receptors and better coupling to intracellular G proteins. This applies for example to the cannabinoid CB1 receptors.

Preferably, the lipid fraction of the nutritional composition comprises 1-10 wt % of marine oil in order to help proper processing and distribution of serotonin receptors in the body of the person that is suffering from a mood or behavioural disorder. In particular the lipid fraction contributes to the effect of the product to redistribute 5HT1A receptors over neurons and the internalization of 5HT2 receptors in neurons, the relative expression of serotonin receptors over the organs and the vesicle-mediated release of neurotransmitters, like serotonin.

In an embodiment, the nutritional composition comprises a source of docosahexaenoic acid (DHA) or eicosapentaenoic acid (EPA).

In a preferred embodiment the weight ratio of eicosapentaenoic (EPA)- and docosahexaenoic acid (DHA) in the product is larger than 0.8, more preferably 1.0 to 30, more preferably 2.0 to 20.

Instead of the pure fatty acids also equivalents can be used which are suitable for use in medical food and include salts, esters and ethers, including glyceride and phospholipid forms, as known in the art. When making calculations about amounts, one can assume the same bioavailability as the pure fatty acid and a contribution of fatty acid that is similar to the amount moles of fatty acids in the complete molecule, and correcting for the weight of the complete molecule.

One important property of the lipid fraction is its ability to contribute to the low satiating properties of the ready to use product. In an advantageous invention the nutritional composition of the invention is suitable to induce a relatively high ghrelin response after (oral) consumption of the product. In order to contribute to this characteristic the lipid fraction comprises per 100 g preferably more than 2 g octanoic acid (=C8:0) and more preferably 4 to 40, most preferably 8 to 20 g of octanoic acid or its equivalents (all based on total lipid content). Equivalents of octanoic acid are those chemical substances which when consumed by humans increase the concentration in blood of compounds which comprise octanoic acid, such as triglycerides. Examples of equivalents of octanoic acid are salts of octanoate, esters or ethers of octanoic acid like acetyl-octanoate or butyl-octanoate or triglycerides. Refined medium chain triglyceride oil was found to be a good source of endogenous octanoic acid.

The selection of amount and type of the lipids in the lipid fraction preferably contributes to the relatively low postprandial CCK- and PYY response after consumption of the product. This is achieved because the lipids are easily digestible and form the right micelles in the duodenum after release of the bile secretions. This is preferably achieved by including the lipid fraction in the product as small droplets that are homogeneously distributed over the product. It is also preferred to include an emulsifier system which interferes as little as possible with the emulsifying events in the duodenum. That is why the amount of diglycerides and especially monoglycerides is preferably relatively low. In a preferred embodiment the amount of the sum of mono and diglycerides is less than 10, preferably less than 2 wt % of the lipid fraction. The total amount of phospholipids and lyso-phospholipids usually is 0.5-12, preferably 0.7-6, more preferably 0.8 to 4, most preferably 0.8 to 3.4 g per 100 g lipid fraction.

The lipid fraction preferably facilitates modulation of the serotonergic system. It is therefore preferred to include a lipid fraction in the product according the invention which comprises a source of omega-3 long chain polyunsaturated fatty acids [(N-3) LC-PUFA's].

In order to modulate the serotonergic signalling, preferably the weight ratio of long chain polyunsaturated fatty acids (LCPUFA's) of the n-3 class to that of the n-6 class is 0.25-9.4, preferably 0.5 to 4. With long chain fatty acids is meant herein fatty acids having at least 18 carbon atoms. A preferred source of n-3 LCPUFA's is krill oil though more sources of omega 3 long chain poly-unsaturated fatty acids are known in the art, like other marine oils, algae oils, fungal oil and oils derived from or extracted from genetically modified organisms, including genetically modified plants. The way such organisms should be modified to increase the amount of n-3 LCPUFA's during their life is known in the art and can include introduction of genes with increased elongase- and/or desaturase activities in these organisms.

The content of the lipid fraction in a nutritional composition of the invention is usually at least 2 g per 100 g of the total nutritional composition, in particular at least 3 g per 100 gram, more in particular at least 5 g per 100 g. The content, in particular in a ready-to-eat product, is usually less than 50 g per 100 g, in particular 40 g per 100 g or less, more in particular 24 g per 100 g or less.

For a liquid product, the lipid content is preferably in the range of 1.2-5 g/100 g of the composition, more preferably 2 to 4 g per 100 g ready to drink product.

For a semi-solid product the lipid content is preferably in the range of 4 to 24 g/100 g of the composition. For a solid product the lipid content is preferably in the range of 8-40 g/100 g of the composition.

Mineral Composition:

Optionally, the nutritional composition comprises a mineral. The amount of minerals in the product can be measured as the amount of mineral ash. In order to provide the proper amount of the active mineral ions, allow a rapid digestion rate of the food constituents and induce the proper postprandial response the amount of ash nutritional product is usually relatively low, at least in the form in which it is intended to be administered ('ready to use'). Preferably the amount of ash per 100 g of liquid nutritional composition, in particular when in a ready to drink product form, is less than 1.8, more preferably 0.7 to 1.7, most preferably 0.8 to 1.6 gram.

In a liquid nutritional composition, the ionic strength of the composition can play a role, in particular with respect to modulating the release of satiating gut hormones. A low ionic strength is thought to prevent too rapid release of such gut hormones. The ionic strength can be measured by determining the osmolarity or osmolality of the liquid product. It is preferred that the product demonstrates an osmolarity of 170 to 340 mOsm/l, more preferably 190 to 310 mOsm/l, most preferably 210 to 290 mOsm/l.

The amount of sodium and potassium in one ready to serve unit should preferably be low, in order to decrease emesis, nausea and activation of EC cells. The amount of sodium ions included in the composition preferably is less than 90 mg per 100 g, preferably 20 to 80 mg per 100 g. This allows a daily consumption of less than 1500 mg per day of total diet.

Zinc content is preferably relatively high in order to increase the amount of ghrelin that is released after consumption of the product. The amount of zinc in the product is preferably more than 2.4, more preferably 3.2 to 24, most preferably 4 to 18 mg per 100 g product. Preferably the magnesium content is higher than 26 mg/100 ml or 26 mg per 100 g of the nutritional composition, in particular in a ready to eat product, more preferably 32 to 48 mg per 100 ml or per 100 g of the nutritional composition, in particular in a ready to eat product, in order to treat deficiencies that are critical in the treatment of the diseases, while eating relatively low amounts of the product according the invention. Magnesium can be included in the product as food grade ingredient as known in the art, for example magnesium sulphate or magnesium bicarbonate.

Iron/copper ratio is preferably high to prevent deterioration in the product and increase metabolic pathways which support serotonin signalling and tryptophan metabolism. Preferably the weight ratio of iron to copper in the nutritional composition, in particular in a ready to use product, is more than 10, more preferably 12 to 40, most preferably 14 to 28. The amount of iron ion in the nutritional composition preferably is in the range 0.1 to 15 mg per 100 g product, more preferably 0.3 to 7 mg per 100 g product, most preferably 0.6 to 3 mg per 100 g product, in particular for a ready-to-drink product. The stated upper limit for the iron is in particular relevant in order to prevent instability in the product and entrance of iron salts in the colon. The iron ions preferably have the form of ferrous ions. The ions must be bound to anions which allow rapid dissolution in the gut and allow high bioavailability of iron. Suitable anions to achieve this are organic acids like sulphate, or gluconate, ascorbate and amino acids, like glycine or alanine.

The buffer capacity of the nutritional composition can be measured by methods known in the art, which include titration of composition, in particular in a ready to use product form, and measuring the amount of acid or alkali equivalents which are needed to change the pH value of the product one unit. In a preferred embodiment the buffer capacity of the product is especially low in the pH range 2 to 7.4. This is preferably achieved by selecting ingredients with a low buffer capacity. This applies to the macro-ingredients, for example the proteins, but also to the type of minerals. The type of anions is therefore not an organic acid or phosphate, which are known to have a high buffer capacity. Instead sulphate, chloride or nitrate, or to a small extent, bicarbonate is used as counter ion in the mineral salts. In a preferred embodiment of the mineral fraction of the nutritional composition according the invention is the weight amount of the sum of sulphate and nitrate 0.05 to 20, preferably 0.08 to 2 times the weight amount of phosphates. The weight amount of phosphates is the anion part of the mineral-phosphates that are included in the product. The concentration of phosphorus in the product is defined by applying the criterion that preferably is less than 14 mg per g protein fraction.

Other Components

Several other components are useful to improve the effect of the active ingredients. According the inventors in particular one ore more other components may be included to maintain or improve the action of the most relevant endogenous proteins involved in tryptophan catabolism and serotonin handling, in vivo. These proteins include aromatic L-amino acid decarboxylase, kynurenine hydroxylase, and the expression or localization of one or more serotonin receptors and proteins involved in the release of neurotransmitters, like serotonin, but also dopamine.

Though the purpose of the invention in particular resides in improving a serotonergic signalling system in the brain, and tryptophan is the major precursor compound in de novo serotonin biosynthesis, the inventors believe that prevention of accumulation of undesirable metabolites of tryptophan, which are known as members of the catabolic kynurenine pathway, is beneficial in the treatment of negative emotions or introvert behaviour. Without wanting to be bound by theory, this may not only be because of the effect of the product on the magnitude wherein tryptophan is used for local 5HT biosynthesis, but also because of the effects on the concentrations of tryptophan catabolites which affect cholinergic—(by interaction with the alpha 7 nicotinergic receptor or the acetylcholine binding protein) or glutamatergic neurotransmission (by interaction with the NMDA receptor). In this context it is important to note that some of the catabolytes of tryptophan, like NAD+ (the oxidized form of nicotinamide dinucleotide), may even be beneficial to the function of neurons, astrocytes or microglia.

Accordingly, in a preferred embodiment, a composition (for use in the treatment of negative emotions and introvert behaviour comprises folate (vitamin B11). The content/dosage is preferably relatively high in order to allow rapid catabolism of tryptophan through the kynurenine pathway when needed, and subsequently stimulate neurogenesis and synaptogenesis and microglia function. The inventors believe that the latter phenomena can be explained by the improvement of nucleotide metabolism by the product according the invention. Folate can be included in the product in a form that increases systemic folate concentrations after oral administration. These forms include food grade qualities of folate monoglutamate, folinic acid and one-carbon-substituted folates and polyglutamate forms of these folates. The amount of folate in one dose of (ready to serve) product according the invention is preferably 0.05-4, preferably 0.1-3 times the recommended daily allowance values of the FDA 1989.

Vitamin B6 is preferably included in a composition (for use) according to the invention, in order to prevent accumulation of undesired metabolites of dietetic tryptophan when catabolised through the kynurenine pathway. Suitable sources of vitamin B6 include pyridoxine, pyridoxamine, pyridoxal and pyridoxal phosphate, in free form or as complex with other molecules like amino acids or peptides. The amounts to include are 0.05 to 4, preferably 0.1 to 3 times the recommended daily allowance values, as disclosed in 1989 by the RDA.

Though the kynurenine pathway is stimulated through inclusion of folate and vitamin B6, and this would result in additional synthesis of nicotinamide nucleotides (NAD+, NADH and NADPH and NADP+), for some subjects it can be advantageous to include vitamin B3 in the products. In particular this is advantageous in the early phases, about the first 14 days, of nutritional management or treatment or therapy of negative emotions and introvert behaviour. Suitable forms of vitamin B3 include niacin (nicotinic acid, NA), its salts or esters, and niacin mononucleotide. Suitable daily dosages are 0.1 to 3, preferably 0.15 to 2 times the daily dosage as recommended per day (RDA, 1989 values).

It is preferred to use niacin (NA) or its salts or esters as source of vitamin B3 above nicotinamide. Though it may induce flushes at lower doses compared to its amide form, and may induce a shorter and more transient increase of systemic NAD+ concentrations, it is preferred because the amide form can freely pass the blood brain barrier and the high concentrations of niacinamide will disturb NAD+ metabolism and choline metabolism in brain, while not being capable of potentially being converted to NAD+ (nicotinamide adenine dinucleotide). It is therefore preferred to keep the dose of vitamin B3 per serving unit below a threshold value of 2 times, preferably below 1.0 times the RDA value, when the source of vitamin B3 is niacin, in order to have an undisturbed and maximal biosynthesis rate of NAD in the brain.

Though the biochemical pathways in the brain are of paramount importance, the inventors believe that the hepatic processes also determine brain serotonin handling due to the passage of kynurenine and 3 hydroxy kynurenine, but not quinolinic acid and kyneninic acid over the blood brain barrier.

Hydroxylation of kynurenine is catalyzed by kynurenine mono-oxygenase (KMO) in rat brain and is a main step away from the KYNA pathway (which is katalyzed by the aminotransferase KAT-2) and into the biosynthesis of quinolinic acid and NAD. The inventors consider it to be advantageous that this step can occur in a sufficient amount and it is therefore preferred to include additional vitamin B2 in the formula. Suitable forms of vitamin B2 include food grade qualities of riboflavin or riboflavin which is non-covalently bound to other molecules like peptides or proteins. The amount to include is usually 0.05 to 4 times, preferably 0.1 to 3 times the recommended daily allowance as disclosed by the FDA in 1989.

In addition food grade bioavailable iron ions may be included in the composition, preferably in an amount of 0.1-10 times the recommended daily allowance as published by the Food and drug administration in the USA in 1989. The amount of iron ion in the nutritional composition preferably is in the range of 0.1 to 15, most preferably 0.3 to 7 mg, most preferably 0.6 to 3 mg per 100 g product, in particular per 100 g ready-to-use product.

The quinolinic acid (QA) pathway could result in toxic amounts of QA. The inventors have aimed to prevent this by increasing the rate of phosphoribosylation of QA by providing support to the 5-phosphoribosyl-1-pyrophosphate (PPRP) synthetase. This is achievable by supporting the generation of adenosine triphosphate (ATP) through the components in the composition, in particular through several of the trace elements (vitamins and minerals) in the composition.

The inventors find it important that digestible carbohydrate fraction in the product provide sufficient reducing equivalents in the form of NADPH+ in order to allow this selective form of the kynurenate pathway. A selective increase of the QA pathway at the cost of the biosynthesis of kynurenic acid (KYNA) may induce an enhanced release of neurotransmitters in general, including dopamine, serotonin, glutamate and gamma-aminobutyric acid, as a consequence of increased activation of nicotinic receptors in the brain. This applies in particular to the homomeric nicotinic receptors, like the homopentamer alpha-7 nicotinic receptor in brain.

The inventors believe that the effect of the product on redox state, so in lowering NADH/NAD ratio in brain facilitates the oxidation reactions in tryptophan metabolism and normalizes the metabolic pattern of metabolites into a situation which is beneficial in the treatment in negative emotions and introvert behaviour.

This applies in particular to the oxidation reactions catalyzed by 3-hydroxyanthranilate dioxygenase and kynurenine 3 mono-oxygenase.

The inclusion of vitamin B6 contributes to the capacity to get rid of excess quinolinic acid wherein catabolism to NAD is impossible or undesired, which may occur in impaired phospho-ribosylation as during energy deficiencies.

Choline or betaine is preferably included in the product, because of the effects of these components on longer term on the function of brain alpha-7 nicotinic acetylcholine receptor signaling, e.g. in the hippocampus or other parts under different conditions which are relevant for treating or preventing negative emotions and introvert behaviour. However, the amount should preferably remain relatively small in order to prevent trimethylamine oxide formation. This is achieved by selecting a concentration range of 12 to 120 mg per 100 g of the nutritional composition (in particular in a ready to serve product).

In addition, preferably a (rapidly available) compound is included which prevents that the microflora of the colon can come into contact with the dietetic choline or betaine. Suitable choline compounds are rapidly absorbed in the small intestine and include choline alfoscerate and citicoline. Salts of choline with organic acids are preferably avoided. However, preferably eutectic solvents of choline chloride with urea, zinc chloride, glycerol or mixtures thereof are included as choline source. These eutectic solvents can be manufactured using procedures known in the art, e.g. by combining the proper molar amounts and blending at the right temperature above the melting point of the eutectic solvent to manufacture. Using a facilitator, like a primary amount of solvent prior to addition of the new reagents is preferred.

The changes in serotonergic systems as induced by a product of the invention also increase the effects of the orally administered inositol compounds. In a particular embodiment according the invention an inositol compound is included in the nutritional composition. The inositol compound can contribute to decrease further negative emotions and introvert behaviour or to empower the effect of orally administered inositos on brain processes, which are also relevant to cognitive and memory-retraction processes. The effect of the addition of an inositol compound to the cereal fibre and tryptophan source according the invention can for example be measured by determining the amount of immobility in a forced swimming test or applying an alternative but accepted test model (see Einat H, Karbovski H, Korik J, Tsalah D, Belmaker R H. Psychopharmacology. 2000; 144: 158-162) In a preferred embodiment the inositol is selected from scyllo-inositol, myo-inositol or chiro-inositol. Suitable sources for these active components include the free substances as isolated from natural sources or the chemically synthesized and purified food grade compounds. Suitable amounts of inositol are about 0.05 to about 1 g inositol per 20 to 120 g of the composition (in particular as ready to serve product). A preferred dosage or preferred amount inositol compound in a serving unit is 0.05-1 g.

The vitamin D content is preferably 1.3 to 40, more preferably 1.8 to 34, most preferably 2.0 to 28 microgram per 100 g of the composition (in particular as ready to eat product) in order to combat deficiencies that are critical in the treatment, while eating relatively low amounts of the product according the invention. As vitamin D ingredient the food grade synthetic compounds or isolates as known in the art can be used. It is preferred to use vitamin D3 as ingredient.

It is preferred that the amount of quinones, in particular PQQ in the ready to serve product is more than 5 mg, more preferably 10-2000, most preferably 20-1000 mg per 100 g composition (in particular as ready to use product).

Ascorbic acid or an equivalent is preferably included to ensure proper intake to ensure support of several oxidation (or hydroxylation) reactions in neurotransmitter metabolism, both in the enteric—and the central nervous system. Suitable equivalents or food grade ingredients, like ascorbyl esters, for example esters with organic acids like fatty acids, acetate, butyrate, amino acids, ethers with carbohydrates and salts or esters of ascorbate, like respectively potassium ascorbate and ethyl ascorbate respectively.

The following table provides preferred dosages of vitamins and miscellaneous ingredients. A product according the invention preferably comprises at least two ingredients of Table 1b, next to folate (vitamin B11).

TABLE 1b

| Ingredient/ component | Preferred source | Preferred Amount (x RDA 1989) per serving size |
|---|---|---|
| Vitamin B11 | Non-methylated mono-glutamate forms | 0.05 to 4 |
| Vitamin B6 | pyridoxamine | 0.05 to 4 |
| Vitamin B3 | Niacin (nicotinic acid) | 0.1 to 2 |
| Inositol | Myo-inositol | 0.05 to 1 g |
| Choline, betaine | Eutectic fluids of choline, choline alfoscerate citicoline | 12-120 mg |
| quinones | PQQ, menaquinones | 0-2000, more preferably 5-2000 mg |
| Osmolality | | 210-290 mOsm/l |
| Vitamin D | Vitamin D3 | 18-40 ug |
| Iron | Ferrous sulphate, ferrous gluconate, ferrous chelates with amino acids | 0.5-15 mg |
| cholesterol | Cholesteryl esters, cholesterol | 0-2000, more preferably 10-900 mg |
| Vitamin C | Ascorbic acid, its salts in oxidized or reduced form, ascorbyl esters. | 0.02 to 6, more preferably 0.1 to 3 |

Advantageously, after consumption of a liquid product, the product should remain fluid once it has entered the stomach or ileum in order to allow rapid mixing with digestive juices, which include proteases, amylases lipases and buffering agents. This allows rapid digestion of components of the product and absorption of the active components by the first part of the GIT.

It is preferred to bring the product in a taste which is appreciated by the consumer and supports food consumption. This is preferably achieved by decreasing the activation of vanillin receptors. In a preferred embodiment the amount of vanillin is that low that activation does not occur in a relevant or significant degree, e.g. by avoiding the inclusion of vanilla flavours in the product according the invention.

Product Form, Energy Density, Dosing Unit Size,

The fibre, combination or nutritional composition (for use) according the invention can be used as food supplement or as product for therapeutic- or pharmaceutical intervention. The nutritional composition can be also be provided in the form of a complete nutrition. The fibre, combination or nutritional composition can be provided in any product form, in particular as a ready-to-use product or as a concentrate that is diluted, e.g. with water or by blending it with another a food product.

The products can have a liquid, semi solid or solid nature, depending on palatability requirements or desires of the intended user.

In particular in a liquid product, the fibre fraction, in particular the cereal fibre, preferably imparts a relatively a low viscosity, when dispersed or dissolved. This allows a high palatability of the product and thus compliance. Preferably, the fibre will not cause a significant increase of viscosity of the luminal contents. In addition, the low viscosity allows rapid digestion of the food components and their rapid absorption. The low viscosity does not impair a proper neuro-endocrine response due to free interaction of luminal contents with the gut epithelium.

In accordance with the present invention, liquid products are typically products that are pourable (at 20° C.), in particular pourable from an opened container in which they are contained, or that can be withdrawn from a container by sucking (by a person consuming the liquid) through a straw or drunk directly from an opened container. In particular, a product is considered to be liquid or pourable if its viscosity, as measured using the method as described in the definitions section, lies below 200 mPa·s. Within the context of the invention, the viscosity is the viscosity as measurable using an Anton Paar Physica MCR301 rheometer with a CP50-1/PC cone (diameter 50 mm, 1° difference between middle and outside) at 20° C. at 100 s$^{-1}$. In particular for a liquid product that is intended for administration by drinking, or via a straw or tube, the viscosity preferably is 100 mPa·s or less. In a particularly preferred embodiment, the viscosity is 40 mPa·s or less. In a preferred embodiment, the viscosity of a liquid product according the invention as stored before consumption is 1 to 24 mPa·s, in particular 1-20 mPa·s.

As used herein 'semi-solids' generally are nutritional products comprising 20 to 82 wt % dry mass, in particular 25-75 wt. %. Dry mass is defined as the amount of product that remains after drying under the conditions as recommended for that particular food product according to recognized methods as e.g. published most recently, prior to the effective filing date of the present disclosure by the American Organization of Analytical Chemists. In particular, semi-solids have a viscosity that exceeds the viscosity of a liquid product. Typical examples of semi-solids are puddings, gels, porridges, ice-cream, sandwich spreads, pastes, and products having a similar rheological consistency.

As used herein solids are products comprising less than 18 wt % of water. Typical examples of solids are powders, food-bars (such as granola bars, candy bars), and the like.

A product (for use) according the invention, in particular a nutritional composition, usually has an energy density (ED) in a specific range in order to provide the efficacy without the adverse effects on the intestinal systems. For liquid products the ED is usually more than 1.6, preferably at least 3.2 kiloJoule per gram product, in particular per gram ready to use product.

In a preferred embodiment, the nutritional composition of the invention, in particular a ready to use product or a concentrate, has an energy density of more than 1.67 kJ per gram product, in particular of 3.14 kJ per gram or more, the composition comprising a tryptophan source providing more than 2 mg tryptophan per gram of the total composition, preferably 3-60 mg tryptophan per gram of the total composition;

a peptide comprising at least 7 amino acids, which peptide may be a tryptophan source; and a dietary fibre fraction comprising dietary fibre molecules as mentioned herein.

In particular for a ready-to-eat liquid product, the ED may in particular be 6.7 kJ/g or less, more in particular 4.6 kJ per g or less.

If the product is semi-solid, in particular when having a dry matter content of 20-60 g per 100 g (ready to serve) product, the ED is preferably in the range of 19.2 to 52.8, preferably 26.3 to 46.1 kJ per 100 g (ready to serve) product.

The energy density of the solid product should generally be less than 20 kJ per g (ready to serve) product.

If the nutritional composition is to be used as a (significant part of the) diet by the subject to be treated with the composition, the ED should generally exceed the minimum value of 3.2 kJ/g because it should provide energy to the patient to prevent a lack of glucose or other metabolic energy substrates in blood or tissue, which would support prevalent catabolic processes and the subsequent loss of lean body mass. This overall decrease of catabolism is relevant for tryptophan and serotonin metabolism, because during muscle catabolism branched chain amino acids will be released into the blood, which may impair tryptophan passage over the blood brain barrier. Subsequent conversion of tryptophan into serotonin in the brain can become less, due to lack of substrate. This adverse effect is avoided or at least reduced by a sufficiently high ED.

The decrease of catabolic reactions is in particular achieved by a combination of technical features as claimed, so not only by energy density. It is contemplated that a product of the invention may in particular have an ability to decrease the degree of phosphorylation of PKR or eIF2-alpha, which decreases the degree of ubiquination of intracellular proteins through interaction with FOXO or NFkappaB.

Bad eating practices are a major problem in the group of persons which suffer from negative emotions and introvert behaviour, e.g. ASD children and part of the depressed persons. However, these practices predominantly relate to food quality and not to overall energy consumption. That is why the low minimum will be sufficient in this target group.

The components in the product therefore preferably support energy metabolism and the induction of a beneficial epigenetic condition of nuclear histones to allow a sufficient rate of transcription of the genes of microglia and intestinal immune cells and of neurons that are relevant to for example immune function and the biosynthesis of enzymes involved in tryptophan metabolism and of neurotransmitter receptors.

The maximum value for the ED is usually determined considering the volume of product that should be consumed in order to induce the efficacy as claimed, while both ED and the amount of food that is consumed determine the postprandial physiological response to the consumption activity. This response includes a volume-related response of the GIT through activation of the ENS or entero-endocrine system, which not only regulates digestion, but also satiety and food intake. Therefore values of the energy density of the product preferably are to be considered in combination with the relatively low volumes that are consumed per consumption event. By adding new consumption events with again low volume portions, the efficacy that is aimed for can be obtained.

Conventional food products are typically packed in all possible sizes in order to suit the needs of customers. In the present invention the volume is preferably restricted and coupled to the maximal energy density in order to achieve the efficacy.

Thus, in an advantageous embodiment of the invention, the amount of food and energy that is consumed per serving does not exceed a certain threshold value. This value is determined by the subject's capacity to digest the food properly, and to prevent activation of an excessive postprandial 5HT response in the lower gut, and to prevent activation of the release of a wide range of anorexic peptides, like PP, PYY and others.

In a specific embodiment the amount of the composition which is administered does not exceed 510 kJ per serving size and preferably is in the range of 65 to 9380 kJ, more preferably 75 to 294 kJ. This can be achieved by packaging a ready to use amount in a package size which is sufficiently small. In order to have a convenient package size, this should not be too small, i.e. more than 5 g, preferably 12-130 g, more preferably 18-90 g, most preferably 20-70 g for liquid and semi-solid products. Administration of the active components in a solid matrix is usually provided in a small size, so less than 10, preferably less than 5 g per serving size, in order to prevent overeating which would impair digestion rate and induce activation of the EC cells in the lower parts of the GIT. In addition the solid products have preferably been prepared such that the serving units rapidly will disintegrate once they enter the stomach. Disintegration should preferably not be achieved by using inclusion of highly buffering substances.

The components in the product determine in what form energy is provided to the organism and details will be described in the relevant clauses.

In a preferred embodiment, the nutritional composition is a ready-to-eat product, i.e. a product that is suitable for consumption without adding further ingredients or further processing (except for additional heating to a desired serving temperature). Examples of preferred embodiments are liquids and extruded dry products or bars.

In another preferred embodiment, the nutritional product is a concentrate, which is intended for reconstitution in water or another drinkable liquid or for blending with another nutritional product.

In a specific embodiment, the product is a sterilized liquid or semi-liquid product, in particular a product sterilised with UHT (so above 121 C) at pH2-7.5, preferably 2.6-7.0.

The invention further relates to a packaging, in particular a unit-dose packaging, comprising 5-300 g, preferably 12-130 g of a liquid or semi-solid nutritional composition according to the invention.

The invention further relates to a packaging, in particular a unit-dose packaging, comprising 0.5-10 g of a solid composition according to the invention.

In accordance with the present invention, liquid products are typically products that are pourable (at 20° C.), in particular pourable from an opened container in which they are contained, or that can be withdrawn from a container by sucking (by a person consuming the liquid) through a straw or drunk directly from an opened container. In particular, a product is considered to be liquid or pourable if its viscosity, as measured using the method as described in the definitions section, lies below 200 mPa·s. Within the context of the invention, the viscosity is the viscosity as measurable using an Anton Paar Physica MCR301 rheometer with a CP50-1/PC cone (diameter 50 mm, 1° difference between middle and outside) at 20° C. at 100 s$^{-1}$. In particular for a liquid product that is intended for administration by drinking, or via a straw or tube, the viscosity preferably is 100 mPa·s or less. In a preferred embodiment, the viscosity of a liquid product according the invention as stored before consumption is 1 to 24 mPa·s.

As used herein 'semi-solids' are nutritional products comprising 32 to 82 wt % dry mass. Dry mass is defined as the amount of product that remains after drying under the conditions as recommended for that particular food product according to recognized methods as e.g. published most recently by the American Organization of Analytical Chemists. In particular, semi-solids have a viscosity that exceeds the viscosity of a liquid product. Typical examples of semi-solids are puddings, gels, porridges, ice-cream, sandwich spreads, pastes, and products having a similar rheological consistency.

As used herein solids are products comprising less than 18 wt % of water (moisture). Typical examples of solids are powders, food-bars (such as granola bars, candy bars), and the like.

Method of Treatment

The invention further relates to a method for prophylactic or therapeutic treatment of an impairment of a serotonergic system in the central nervous system, a negative emotion, introvert behaviour, a pervasive disorder, a clinical depression or major depression comprising administering to a subject in need thereof an effective amount of a dietary fibre, combination or nutritional composition according to the invention.

In an embodiment, in the method of treatment, the dietary fibre, combination or nutritional composition is administered in a dosage providing 502 kJ or less, in particular in a dosage providing 20.9-502 kJ.

In an embodiment, in the method of treatment the subject in need thereof, is a human, preferably a human having an age of at least 1 years, in particular a human having an age of 2 to 85 years.

In particular, in a method according to the invention the dietary fibre, combination or nutritional composition is administered orally or administered into the gastrointestinal tract in another way, such as by tube-feeding.

When referring herein to a treatment, this generally includes prophylactic treatments and therapeutic treatments, unless specified otherwise. A prophylactic (preventive) treatment generally is aimed at reducing the chance that the treated subject develops a trait, impairment, symptom, disease, syndrome or disorder. The effectiveness of a prophylactic treatment can e.g. be determined by comparing the probability that a specific trait (etc to disorder) develops in a sufficiently large in a double blind way according the principles of Good Clinical practices, wherein one part of the group is treated according to the invention and another part is treated with a placebo for a relevant period of time. The skilled person will be able to define suitable conditions for the study, depending on the intended effect.

EXAMPLES

Example 1

Ready to eat semi-solid product (pudding, porridge or ice cream or sandwich spread or paste or sauce). In particular suitable for treating autism. The product can in particular be used by toddlers & children in the age range of 1-12 year in amounts which are voluntarily acceptable.

TABLE 2

| Components<br>Dry matter is 25 to 75 g per 100 g product | Quantity per<br>100 g ready<br>to eat product |
|---|---|
| Protein fraction<br>Of which intact protein 5-19.9 g<br>Tryptophan as free amino acid or peptide = 0.1-3 g | 8-20 g |

TABLE 2-continued

| Components<br>Dry matter is 25 to 75 g per 100 g product | Quantity per<br>100 g ready<br>to eat product |
|---|---|
| Digestible carbohydrates<br>Of which maltodextrins are less than 90 wt %<br>Glucose/fructose syrup less than 80 wt %<br>Lactose or galactose or banana puree >2 wt %<br>The sum of isomaltulose, trehalose and<br>isomaltose >2 wt % | 8-20 g |
| Lipids<br>Of which marine oil 1-10 wt % and phosphatidylcholine<br>is <41 wt % | 8-24 g |
| Fibre:<br>Cereal fibr xylan enriched fractions<br>Of which beta-glucans are >1 wt %<br>Acetogenic fibres like inulin and fructo-<br>oligosaccharides are less than 85 wt % of fibre fraction | 6-24 g |
| Vitamin blend comprising at least<br>vitamin D | 2-30 microgram |
| PQQ | 20-1000 mg |
| Mineral premix comprising at least<br>magnesium<br>Optional manufacturing aids, colorants, flavours etc.<br>Water makes up the final weight of the product | 6-20 mg |

Example 2

Dry product. In particular suitable for treating a major depression (moisture content is less than 14 wt % in the ready to use product). The product can in particular be used by an adult.

TABLE 3

| Components; Dry matter is 86-98 g per<br>100 g product; the remainder being water | Quantity per<br>100 g ready<br>to eat product |
|---|---|
| Protein fraction<br>Of which intact protein 11-39.6 g<br>Tryptophan as free amino acid or as dipeptide = 0.4-3 g | 14-40 g |
| Digestible carbohydrates<br>Of which maltodextrins are less than 90 wt %<br>Glucose/fructose syrup less than 80 wt %<br>banana puree<br>The sum of isomaltulose, trehalose and<br>isomaltose >2 wt %<br>Starch >2 wt %<br>fruit may provide some glucose and fructose | 16-70 g |
| Lipids<br>of which marine oil 1-10 wt % | 8-40 g |
| Fibre:<br>Cereal fibre fractions<br>Of which beta-glucans are >1 wt % and xylans are >60%<br>Acetogenic fibres like inulin and fructo-<br>oligosaccharides are less than 35 wt % of fibre fraction | 6-40 g |
| Vitamin blend comprising at least<br>vitamin D | 2-30 microgram |
| Mineral premix comprising at least<br>magnesium<br>Optional manufacturing aids, colorants, flavours etc.<br>Water makes up the final weight of the product | 6-20 mg |

Example 3

Liquid product. In particular suitable for nutritional management of a pervasive symptom

TABLE 4

| Component Energy density = 2.5 to 6.8 kJ/ml | Concentration per 100 g ready to use product (density = 1.1 g/ml) |
|---|---|
| Protein<br>Comprising 5-95 wt % proteins from whey or vegetable<br>origin and more than 1 wt % added free L-tryptophan | 5-9 g |
| Lipids<br>Of which DHA is 0.5-4 g per 100 g fatty acids<br>Rape seed lecithin is 10-40 wt % | 2-5 g |
| Fibre<br>Rice fibre wt 60%<br>partially hydrolyzed guar gum 20 wt %<br>acacia gum (hydrolyzed 20 wt %) | 2-15 g |
| Digestible carbohydrates | 4-12 g |
| Miscellaneous<br>Vitamin and mineral premix complying with the claim requirement | |

Example 4

Product for Testing the Effect of the Product on Introvert Behaviour and Negative Emotions in Allergic Mice

TABLE 5

Ingredients used to modify the standard AIN93-M diet of mice are given below (amounts are given per kg diet).

|  | ACTIVE | CONTROL |
|---|---|---|
| Alanine | 2.9172 | 15.61144 |
| Arginine | 3 | 7.25826 |
| Asparagine | 17.5032 | 0 |
| aspartic acid | 13.0884 | 12.2737 |
| Cysteine | 10.5924 | 3.16114 |
| Glutamine | 7.9872 | 0 |
| glutamic acid | 12.8544 | 37.1743 |
| Glycine | 4.914 | 5.75716 |
| Histidine | 5.0856 | 3.72626 |
| Isoleucine | 11.466 | 7.43486 |
| Leucine | 19 | 23.24056 |
| Lysine | 19.3908 | 4.09712 |
| Methionine | 5 | 5 |
| Phenylalanine | 7.2228 | 8.7417 |
| Proline | 2.5116 | 15.24058 |
| Serine | 8.034 | 8.7417 |
| Threonine | 9.1104 | 6 |
| Tryptophan | 8.9232 | 1.8543 |
| Tyrosine | 7.9092 | 7.43486 |
| Valine | 7.6752 | 9.28916 |
| total | 184.1856 | 182.0371 |
| (leu + ile + val)/(thr + his + lys) | 1.1356 | 2.8911 |
| trp/(leu + ile + phe) | 0.2368 | 0.04704 |

Carbohydrate Fraction
low glycemic index
Fat Fraction
fish oil higher in EPA than DHA (two options attached as PDFs)
1.5% EPA, 1% DHA
Fibres
Vitamins
Vitamin A and D
B vitamins
the highest possible dose that does not give toxicity problems should be used Experiments:

a/ The product for decreasing negative emotions and introvert behaviour is tested in an animal model, wherein symptoms of negative emotions and introvert behaviour are induced. Models are known in the art and include models wherein a degree of inflammation is created in the gut or wherein specific forms of food-allergy are created. This induces a local increase of the release of proinflammatory cytokines like TNF-alpha, IL-1 beta and IL-6, and in particular IL-6, as well as excessive serotonin release by EC cells and the neurons of the enteric nervous system. This induces for example a higher gut motility, diarrhoea and low appetite.

After administration of the product according the invention the symptoms related to introvert behaviour and negative emotions are measured and the associated gut motility, response to IL-6 and the local release of serotonin.

b/ Immune cells, in particular macrophages or microglia can be isolated from animals suffering from negative emotions and introvert behaviour and tolerizable genes can be analyzed on activity. The degree of methylation of histone H3 at lysine 4 or acetylation of histone H4 can be measured as disclosed by Foster 2007. The product according the invention may induce a lower degree of acetylation and/or a higher degree of methylation and increase the response to IL-6, in particular after repeated exposure to IL-6.

c/ After oral administration of the food product the release of the primary bile acids cholic acid and chenodeoxycholic acid in the duodenum is measured and the degree of activation or expression of the FXR receptor in the intestinal cells in duodenum and proximal parts of the ileum. The use of the product according the invention is thought to induce a lower degree of bile-acid mediated activation of intestinal processes compared to prior art products developed to treat or prevent negative emotions and introvert behaviour.

d/ the effect of free ferulic acid compounds on gut behaviour can be analyzed by adding different amounts of ferulates to the lumen of the gut and investigating gut motility and behaviour of the enteric nervous system and EC cells, in particular with regard to the serotonin-related processes.

Example 5

Diagnosis of a Negative Emotion or Introvert Behaviour

Basic Assumptions and Definitions

1—Emotions are important determinants of behavior, attitude and the state of mind in humans 2—Behavior or state of mind can be considered as a disorder or pathology when its characteristics are considered to be too undesirable in a social context or for the person itself and persist for a longer period of time, without a clear cause can be recognized 3—Clinicians and health practitioners use accepted methods for diagnosing such behavior and classify the behavior as assessed in one of the disorders as agreed and defined in the ICD-10 and DSM-IV or more up to date version thereof.

Negative emotions have been defined in the art and comprise a range of emotions as summarized in the table below.

TABLE 6

| KIND OF EMOTION | POSITIVE EMOTIONS | NEGATIVE EMOTIONS |
|---|---|---|
| EMOTIONS RELATED TO OBJECT PROPERTIES | Interest, curiosity Attraction, desire, admiration Surprise, amusement | Alarm, panic Aversion, disgust, revulsion Indifference, familiarity, habituation |
| FUTURE APPRAISAL EMOTIONS | Hope | Fear |
| EVENT RELATED EMOTIONS | Gratitude, thankfulness Joy, elation, triumph, jubilation | Anger, rage Sorrow, grief |
| SELF APPRAISAL EMOTIONS | Pride in achievement, self confidence, sociability | Embarrassment, shame guilt, remorse |
| SOCIAL EMOTIONS | Generosity Sympathy | Avarice, greed, miserliness, envy, jealousy Cruelty |
| CATHECTED EMOTIONS | Love | Hate |

These emotions can therefore be distinguished from feelings or sensations. Though such emotions manifest themselves in different circumstances, in daily life the negative emotions may become so dominant that they are unacceptable and desire treatment. Several treatment protocols have been suggested in the art and the administration of medication is presently common.

The scoring in part of these negative emotions, in particular in the domains anhedonia, reduced (mental) energy and depressed mood, characterizes the diagnosis of several forms of clinical depression, such as major depression, dysthymia, recurrent depression disorder. Relevant negative emotions are therefore aversion, indifference, sorrow and grief, embarrassment and shame, which all could result in a systematic lack of pleasure or enjoyment of events or common feelings of sadness, or in a significant degree of apathy or lack of initiative and ambition or excessive feelings of tiredness or mental fatigue. The presence of the latter symptoms is often considered to proof the presence of these negative emotions.

When at least two of the domains anhedonia, reduced energy and depressed mood are assessed to be abnormal, the person is considered to suffer from a major depression. For reliable assessment of these domains validated methods are applied as a daily routine and the methods have been described in the art. These include making inquiries about the individual's daily behaviour, thoughts and attitude.

As an example for the diagnosis of dysthymia the situation for the symptoms as given below is assessed.
1. During a majority of days for two years or more, the adult patient reports depressed mood or appears depressed to others for most of the day.
2. When depressed, the patient has two or more of:
   1. decreased or increased appetite
   2. decreased or increased sleep (insomnia or hypersomnia)
   3. Fatigue or low energy
   4. Reduced self-esteem
   5. Decreased concentration or problems making decisions
   6. Feels hopeless or pessimistic
3. During this two-year period, the above symptoms are never absent longer than two consecutive months.
4. During the first two years of this syndrome, the patient has not had a major depressive episode.
5. The patient has not had any manic, hypomanic, or mixed episodes.
6. The patient has never fulfilled criteria for cyclothymic disorder.
7. The depression does not exist only as part of a chronic psychosis (such as schizophrenia or delusional disorder).
8. The symptoms are often not directly caused by a medical illness or by substances, including drug abuse, or other medications.
9. The symptoms may cause significant problems or distress in social, work, academic, or other major areas of life functioning.

The decrease of these negative emotions which are relevant to depression disorders also reduces the risk of suicide in an individual.

Excessive negative emotions which cannot be counterbalanced by positive emotions can also result in other types of diseases and disorders than the depression-type disorders. For example, the emotions alarm, panic and fear contribute to the diagnosis of anxiety disorders, panic disorder, generalized anxiety disorder, social anxiety disorder, obsessive compulsory disorder (OCD) and phobias.

The emotions anger, avarice, cruelty and hate contribute to aggressive and violent behaviour.

Affect disorders are diagnosed by assessing the presence of again a different combination of negative emotions and absence of positive emotions, which would result in the symptom of being incapable of demonstrating affect or in seeking low interactive sociability or an isolated lifestyle or anti-social and even cruel behavior.

The product according the invention therefore aims to decrease the negative emotions as listed, which would decrease the scoring in these domains to a non-pathological degree, which would result in decreasing the degree or severity of the diseases depressive disorders, anxiety disorders, phobias, affect disorders and aggressive or violent behaviour and a reduction of the risk of suicide. The patients will subsequently score better in their behaviour and mood, for example, by enjoying life more, demonstrate a more social behaviour and being more active and showing more initiative in their life. The nutritional management and/or treatment of these negative emotions also improve the capacity of the diseased individual to cope with the events in daily life and decrease the stress they experience by these events. The improvement of negative emotions and introvert behaviour makes the product also suitable for use in the treatment of post-traumatic stress disorder.

The product according the invention further improves introvert behaviour. Introvert behaviour is thought to result from a state wherein the individual is wholly or predominantly concerned with one's own mental life. Introvert behaviour can be a normal phenotype in humans, as becomes clear from the table below.

TABLE 7

|  | Nathan | Beatrice | Dave | Spencer | Anne |
|---|---|---|---|---|---|
| I am the life of the party. | Agree | Agree | Agree | Disagree | Disagree |
| I enjoy being the center of attention. | Agree | Disagree | Agree | Disagree | Disagree |
| I am skilled in handling social situations. | Agree | Agree | Agree | Disagree | Disagree |
| I like to be where the action is. | Agree | Agree | Disagree | Agree | Disagree |

TABLE 7-continued

|  | Nathan | Beatrice | Dave | Spencer | Anne |
|---|---|---|---|---|---|
| I make new friends easily. | Agree | Agree | Disagree | Agree | Disagree |
| I am quiet around strangers. | Disagree | Disagree | Agree | Disagree | Agree |
| I don't like to draw attention to myself. | Disagree | Agree | Agree | Agree | Agree |
| I don't like to party. | Disagree | Disagree | Disagree | Agree | Agree |
| I like to work independently. | Disagree | Agree | Agree | Agree | Agree |
| I often enjoy spending time by myself. | Disagree | Disagree | Disagree | Agree | Agree |
| Score | 100% Extravert | 70% Extravert | 50% Extravert 50% Introvert (Ambivert) | 70% Introvert | 100% Introvert |

However, the introvert behaviour can also take a pathologic form, wherein interactive socialization is avoided, isolation above participation in groups is highly preferred, low affect is demonstrated and very little of the individual's feelings or emotions is shown. The individual may even seem to be non-accessible to external events or does not react or respond to them.

An abnormal or pathologic degree of introvert behaviour can easily be recognized and contributes to the diagnosis of disorders which belong to the autistic spectrum. Introvert behaviour can also be an attribute of the diagnosis of some forms of depression (in the domain apathy and lack of initiatives) or of affect disorders.

The domains negative emotions and introvert behaviour are to be treated by the formula. This is done by the ability of the formulation as claimed to induce one single and useful biological response.

At the same time the product increases serotonin concentration in the brain, prevents excessive serotonin release by the EC cells in the gut and provides a rapid catabolism of tryptophan in central and peripheral compartments. The latter induces only a moderate concentration of astrocytal KYNA in the central synapses which keeps NMDAR activation moderate and at the same time allows ample NAD+ generation to facilitate the function of activated microglia. This increase of NAD+ is mandatory to allow full function of the catabolic systems of activated microglia, thus preventing long term or chronic activation of microglia and excessive destruction of nervous tissue outside the region wherein the pathology is happening which causes the activation.

This not only prevents damage to tissues but also ultimately result in more rapid and better functioning of serotonergic, NMDAR-mediated and alpha-7 nicotine acetylcholinergic signalling and the neuronal systems that depend on the projections of glutamatergic, serotonergic and cholinergic neurons. These nervous systems are involved in the regulation of negative emotions and introvert behaviour. It is known that many parts of the brain are involved in the processing of signals that contribute to negative emotions and introvert behaviour (including limbic system (e.g. amygdala and insula), the periaqueductal gray and hippocampus and cortical and medial prefrontal subregions.

Anxiety: acnp.org/g4/GN401000125/CH123.html and ncbi.nlm.nih.gov/pubmed/19423077

Depression: SSRI are also standard

Phobias/Panic disorder: MAO inhibitors

Autism/introversion: a7-nAChR antagonism: spectracell.com/media/097fullpaper2001ajpcholinergic-activity-in-autism.pdf and utd.edu/~mxa049000/lessons/research/literature/Autism/super%20new/Lippiello%20nicR%20blockers%20for%20autism%20MH%2006.pdf and brain.oxfordjournals.org/content/125/7/1483.full OCD: 5HT: bmu.psychiatry.cam.ac.uk/publications/wenzke04red.pdf Aggression: serotonin-dopamine systems: sciencedirect.com/science/article/pii/S1359178908000438 low serotonin: ncbi.nlm.nih.gov/pmc/articles/PMC14745/

These references indicate a commonality in at least some of the neuropathological problems.

The product is disease-modifying by interfering with the functioning of monoamine signalling in brain.

Example 6

Combined Dietary Intervention with a Tryptophan-Enriched Protein Fraction and an Arabinoxylan-Enriched Fibre Fraction Background Accumulating evidence supports a link between disturbances in the intestinal tract and disturbed behaviour in various disorders including autism. Indeed, a disturbed immune system is demonstrated in autistic patients, while around 30% of the autistic population suffers from intestinal problems. Specifically in the intestinal tract the disturbed immune responses could lead to exacerbations of autistic behavior. A hypersensitivity reaction in the intestinal tract towards allergens like cow milk protein and gluten may therefore contribute to behavioural disturbances. In line with this suggestion, the cow milk allergic (CMA) mouse model has been developed. This is a murine model of autism that is based on the strong link between allergies and autism, which is modulated by the gut-brain axis. CMA mice have disturbed social behavior and are more anxious.

Materials & Methods

For the induction of cow milk allergy (CMA) male mice of the C3H/HeOuJ strain were used. The interaction between CMA and dietary interventions was studied in a 2×4 design, including the factors Model (2 levels: Ctrl and CMA) and Diet (4 levels: Diet1-4, see table 1). Thus, each diet was given to a group of mice in which cow milk allergy was induced (CMA mice) and to a group that only received the cholera toxin (without the allergen) as a control (Ctrl mice).

TABLE

Description of diets.

| Diet 1 | Diet 2 | Diet 3 | Diet 4 |
|---|---|---|---|
| Control AIN-93G diet; amino acid based, providing 1.8 g tryptophan/kg diet; 5% cellulose fibres | AIN-93G diet in which the protein fraction was enriched with tryptophan (total of 5.2 g/kg diet) | AIN-93G diet in which the fibre fraction was enriched with arabinoxylan-containing rice fibers (2% rice fibers + 3% cellulose) | AIN-93G diet with the protein fraction of Diet 2 and the fiber fraction of Diet 3 |

The behavioural consequences of CMA were assessed in tests for negative emotions (novelty-induced grooming) and for introvert behavior (disturbed social interaction).

For the grooming test, single animals were placed in an unfamiliar observation box for 15 min, which usually evokes spontaneous grooming activity. In the CMA mouse model of autism, this novelty-induced emotional response is exacerbated. The duration and number of grooming episodes were recorded during the test to quantify grooming behavior. Data are expressed as percentage of Control values, and analyzed using ANOVA.

For the social interaction test, the test mouse was placed in an open field in which a small cage is placed containing an interaction mouse. The test mouse can see and smell the interaction mouse without having any physical contact. For 5 minutes the mice are placed in the cage and social interaction behavior quantified, starting with the latency time to enter the interaction zone. Latencies to engage in social interaction were analyzed using Mann-Whitney U test.

Results

Emotional disturbances induced by the CMA model and the effects of the dietary interventions are displayed in FIG. 1. The emotional reaction to a novel environment was exacerbated by CMA as indicated by an increased amount of novelty-induced grooming behavior in animals on the control diet (Diet 1: Ctrl vs CMA: $F(1,18)=10.96$, $p<0.005$; *). While both the proteins of Diet 2 and the fibers of Diet 3 slightly reduced the amount of grooming, the combination of proteins and fibers in Diet 4 significantly reduced grooming in CMA animals as compared to CMA animals on the control Diet 1 ($F(1,17)=6.53$, $p<0.03$; **). Diet 4 completely normalized novelty-induced grooming behavior (Diet 4: Ctrl vs CMA: $F(1,17)=0.17$, $p=0.69$; n.s.).

CMA-induced disturbances in social behaviour and the effects of dietary intervention are displayed in the FIGURE below. In animals on the control diet, CMA tended to increase the latency to engage in social interaction ($Z=-1.629$, $p=0.10$; #). Both the proteins of Diet 2 and the fibers of Diet 3 reduced the latency time, but not as effective as the combination of proteins and fibers in Diet 4, which significantly reduced the latency in CMA animals as compared to CMA animals on the control Diet 1 ($Z=-2.512$, $p<0.02$; **). In addition, Diet 4 reduced the latency to engage in social behavior in CMA animals as compared to Ctrl animals (Diet 4: Ctrl vs CMA: $Z=-1.985$, $p<0.05$; *).

CONCLUSIONS

Induction of cow milk allergy (CMA) in male mice resulted in disturbances of both emotional behavior and social behavior. First, CMA increased the level of anxiety in the mice, which resulted in an exacerbation of novelty-induced grooming behavior. Second, CMA promoted the display of introvert behaviors, resulting in an increased latency to start engaging in normal social interactions.

Both CMA-induced behavioural disturbances were affected by dietary interventions with either a tryptophan-enriched protein fraction (Diet 2) or an arabinoxylan-enriched fibre fraction (Diet 3). However, combined treatment with both the protein fraction and the fibre fraction (Diet 4) was most effective in improving CMA-induced behavioural disturbances.

The invention claimed is:

1. A nutritional composition having an energy density of more than 1.67 kJ per gram, with the composition comprising
   a tryptophan source providing 3 mg tryptophan per gram of the total composition or more;
   a peptide having at least 7 amino acid units, which peptide may be a tryptophan source; and
   dietary fibre comprising an arabinoxylan.

2. The nutritional composition according to claim 1, having an energy density of 3.14 kJ per gram or more.

3. The nutritional composition of claim 1 wherein the dietary fiber comprises rice fibre.

4. The nutritional composition of claim 1 wherein the dietary fiber comprises cereal dietary fibre.

5. The nutritional composition of claim 1 wherein the tryptophan source provides 3-60 mg gram tryptophan per gram of the total composition.

6. The nutritional composition of claim 1 wherein the tryptophan source comprises free tryptophan, a salt thereof, an ester thereof, or a dipeptide comprising a tryptophan unit.

7. The nutritional composition of claim 1 comprising a docosahexaenoic acid (DHA) source.

8. The nutritional composition claim 1 comprising a digestible carbohydrate fraction, wherein the glycaemic index of the digestible carbohydrate fraction is less than 80.

9. The nutritional composition of claim 1 wherein
   the ratio of tryptophan to large neutral amino acids is at least 0.22.

10. A unit-dose packaging, comprising 5-300 g of a liquid or semi-solid nutritional composition having an energy density of more than 1.67 kJ per gram, with the composition comprising
    a tryptophan source providing 3 mg tryptophan per gram of the total composition or more;
    a peptide having at least 7 amino acid units, which peptide may be a tryptophan source; and
    dietary fibre comprising an arabinoxylan.

11. A unit-dose packaging, comprising 0.5-10 g of a solid composition having an energy density of more than 1.67 kJ per gram, with the composition comprising
    a tryptophan source providing 3 mg tryptophan per gram of the total composition or more;
    a peptide having at least 7 amino acid units, which peptide may be a tryptophan source; and
    dietary fibre comprising an arabinoxylan.

* * * * *